US012654167B2

(12) United States Patent
Swami et al.

(10) Patent No.: US 12,654,167 B2
(45) Date of Patent: Jun. 16, 2026

(54) PERFUSABLE HYDROGEL MICROCHANNEL SHELL AND METHODS THEREOF

(71) Applicant: University of Virginia Patent Foundation, Charlottesville, VA (US)

(72) Inventors: Nathan Swami, Charlottesville, VA (US); Walter Varhue, Glen Allen, VA (US); George Christ, Crozet, VA (US); Shayn Peirce-Cottler, Charlottesville, VA (US); Aditya Rane, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 962 days.

(21) Appl. No.: 17/451,256

(22) Filed: Oct. 18, 2021

(65) Prior Publication Data
US 2022/0118446 A1     Apr. 21, 2022

Related U.S. Application Data

(60) Provisional application No. 63/092,630, filed on Oct. 16, 2020.

(51) Int. Cl.
| | |
|---|---|
| *B01L 3/00* | (2006.01) |
| *C12M 1/12* | (2006.01) |
| *C12M 3/00* | (2006.01) |
| *C12M 3/06* | (2006.01) |
| *C12N 5/071* | (2010.01) |

(52) U.S. Cl.
CPC ....... *B01L 3/502715* (2013.01); *C12M 21/08* (2013.01); *C12M 23/16* (2013.01); *C12M 25/14* (2013.01); *C12N 5/0697* (2013.01); *B01L 2300/069* (2013.01); *B01L 2300/161* (2013.01)

(58) Field of Classification Search
CPC ......... B01L 3/502715; B01L 2300/069; B01L 2300/0161; C12M 21/08; C12M 23/16; C12M 25/14; C12N 5/0697; C12N 5/0068; C12N 2533/30; C12N 2535/10
See application file for complete search history.

(56) References Cited

U.S. PATENT DOCUMENTS

| | | | |
|---|---|---|---|
| 2016/0139110 A1* | 5/2016 | Zantl | G01N 33/5029 435/287.1 |
| 2019/0217291 A1* | 7/2019 | Hou | C12M 29/10 |
| 2019/0314814 A1* | 10/2019 | Dorfman | C12N 15/1003 |

* cited by examiner

*Primary Examiner* — Michael L Hobbs
(74) *Attorney, Agent, or Firm* — Schwegman Lundberg & Woessner, P.A.

(57) ABSTRACT

A microfluidic device can include a superstructure defining a microfluidic channel therein and a first hydrogel bonded to the microfluidic channel to define a perfusable channel therein, the first hydrogel including cells embedded therein or thereon. The microfluidic device can optionally include a second hydrogel bonded to the microfluidic channel or to the hydrogel.

20 Claims, 20 Drawing Sheets

1: The Lumen Imprint and Microchannel are Replicated by Soft Lithography
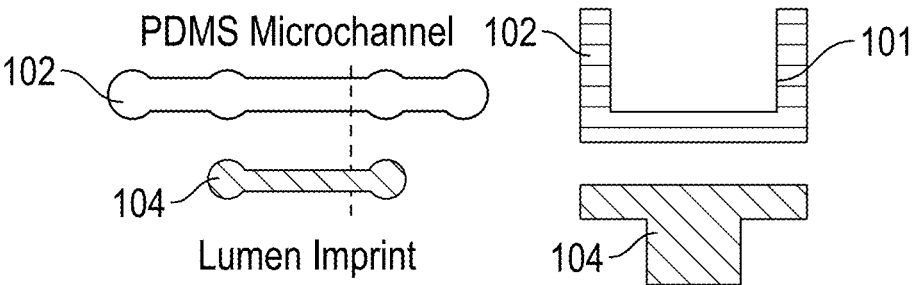
2: The Lumen Imprint is Aligned Within the Microchannel
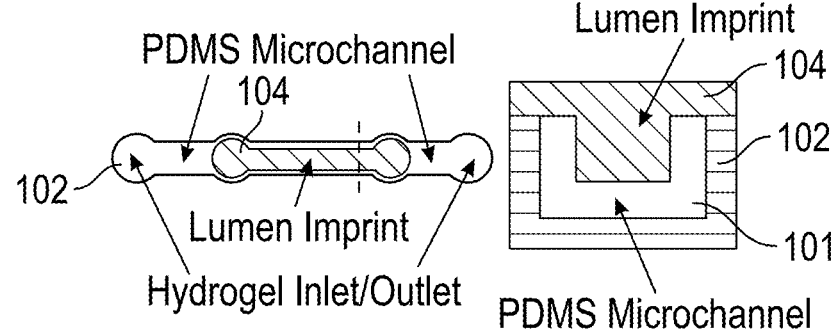
3: Hydrogel is Introduced to the Channel and Cross-linked
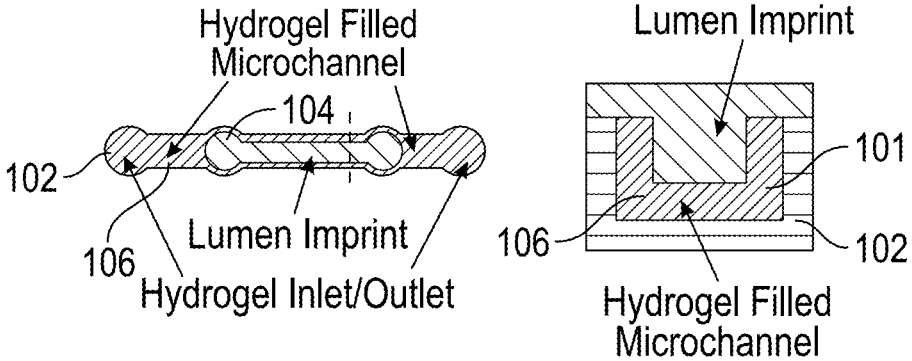
4: Lumen Imprint is Released Leaving a Perfusable Microgel
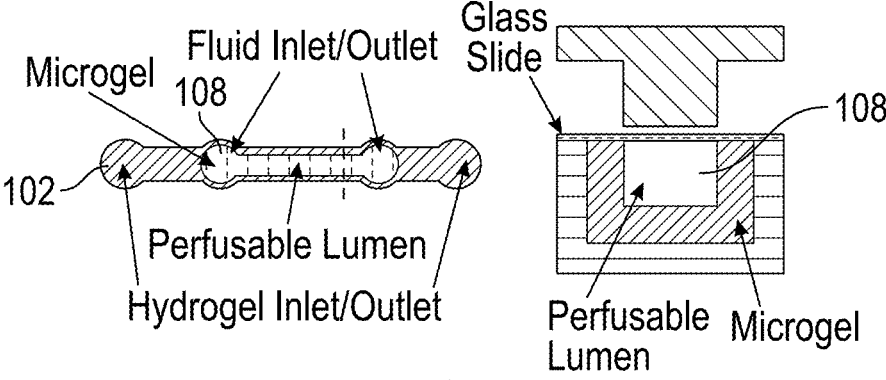
FIG. 2A

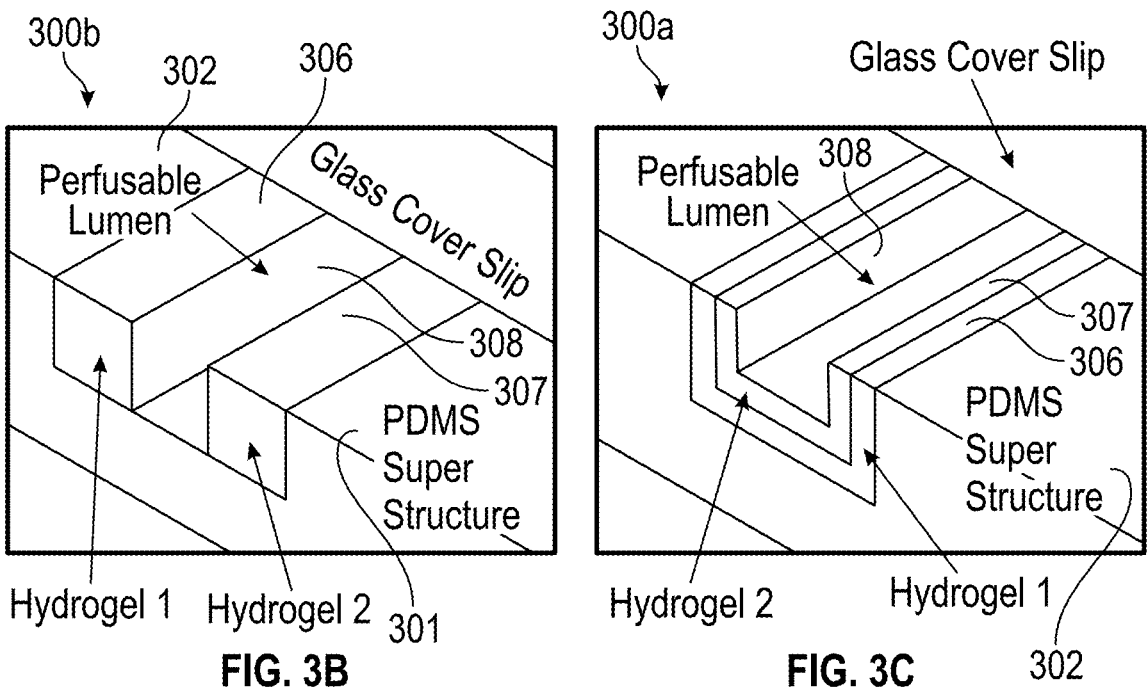
FIG. 3B
FIG. 3C
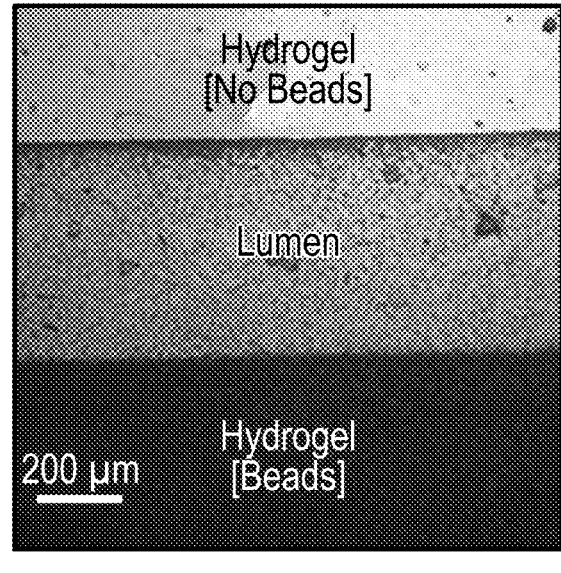
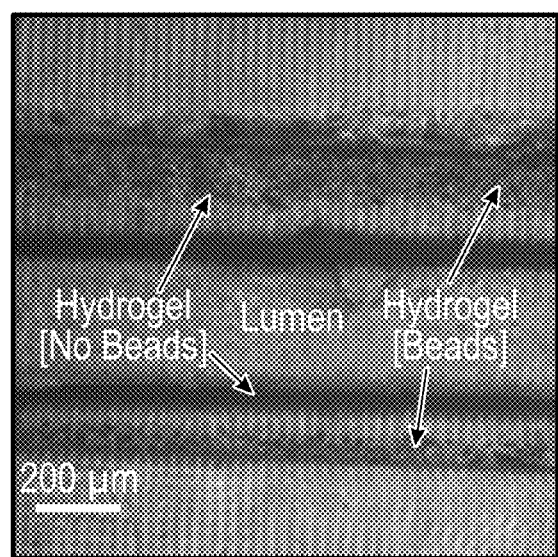
FIG. 3D
FIG. 3E

1: Realignment Guides for the 2nd Imprint are Drilled and the 1st Imprint Process is Completed
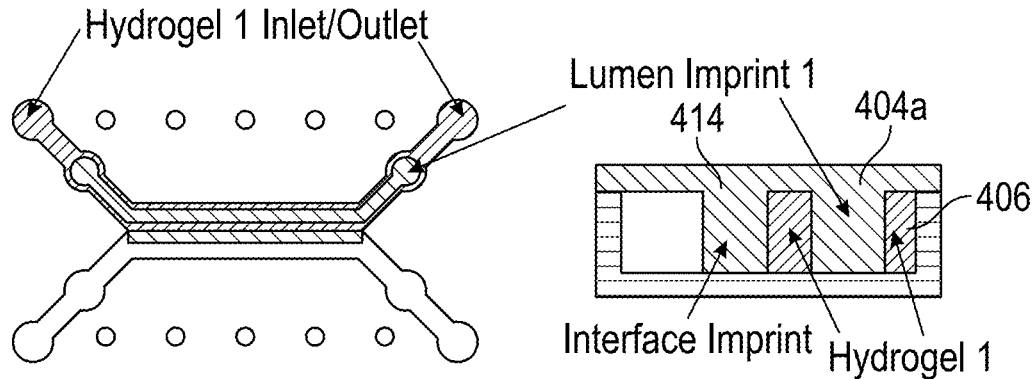
2: Using the Guides the 2nd Lumen Imprint is Re-aligned
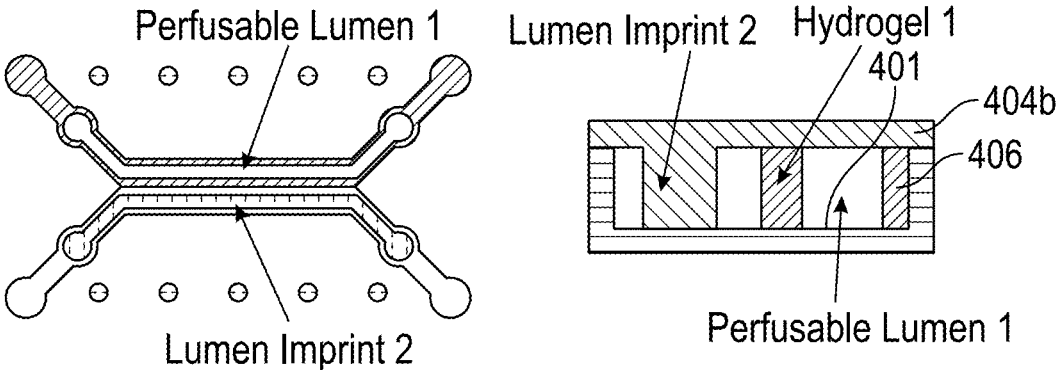
3: The 2nd Hydrogel is Introduced and Cross-linked Forming a Hydrogel/Hydrogel Interface
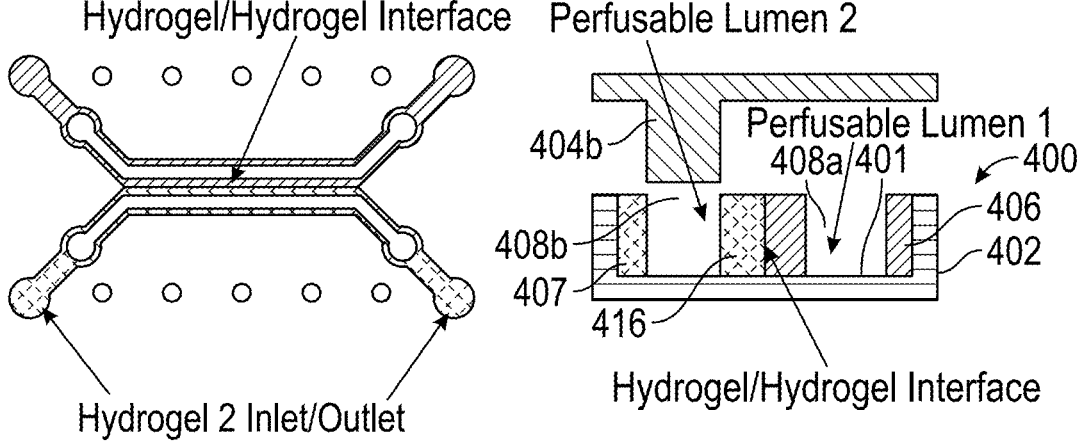
FIG. 4A

FIG. 5H                    FIG. 5I
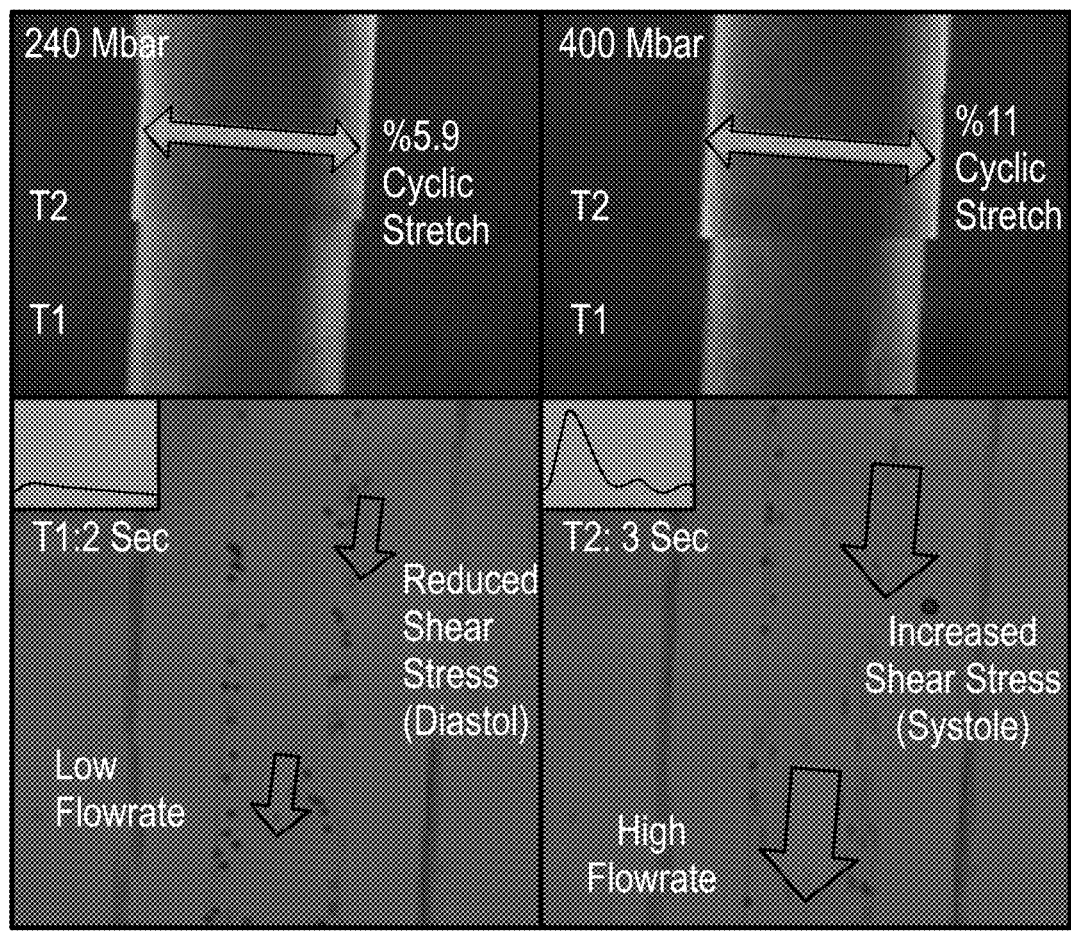
FIG. 5J                    FIG. 5K
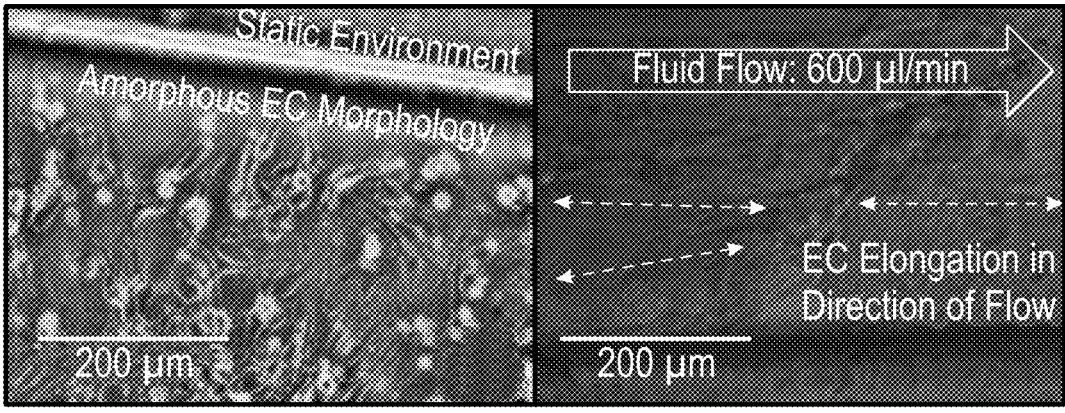
FIG. 5L                    FIG. 5M FIG. 7A                               FIG. 7B
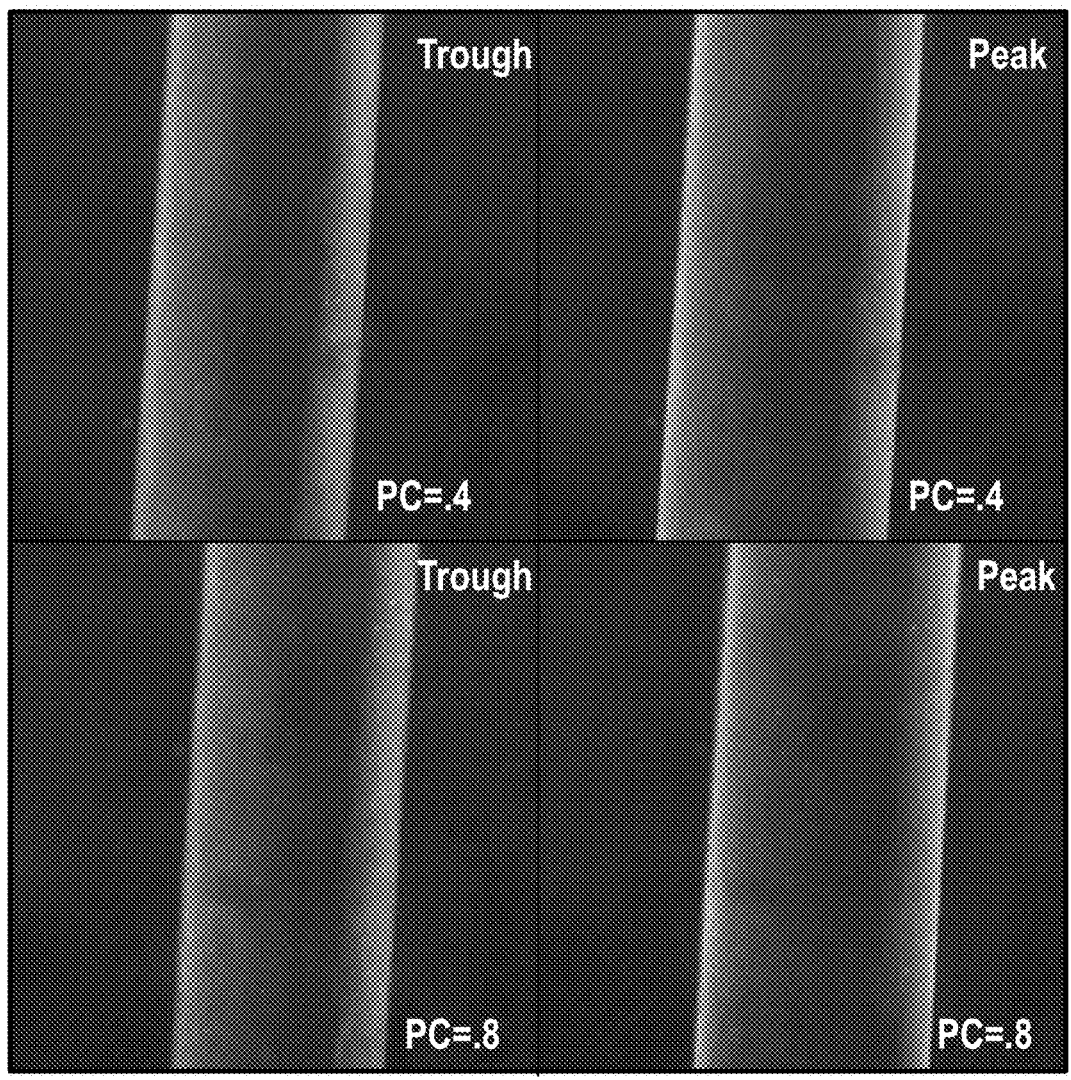
FIG. 7C                               FIG. 7D FIG. 8A                    FIG. 8B
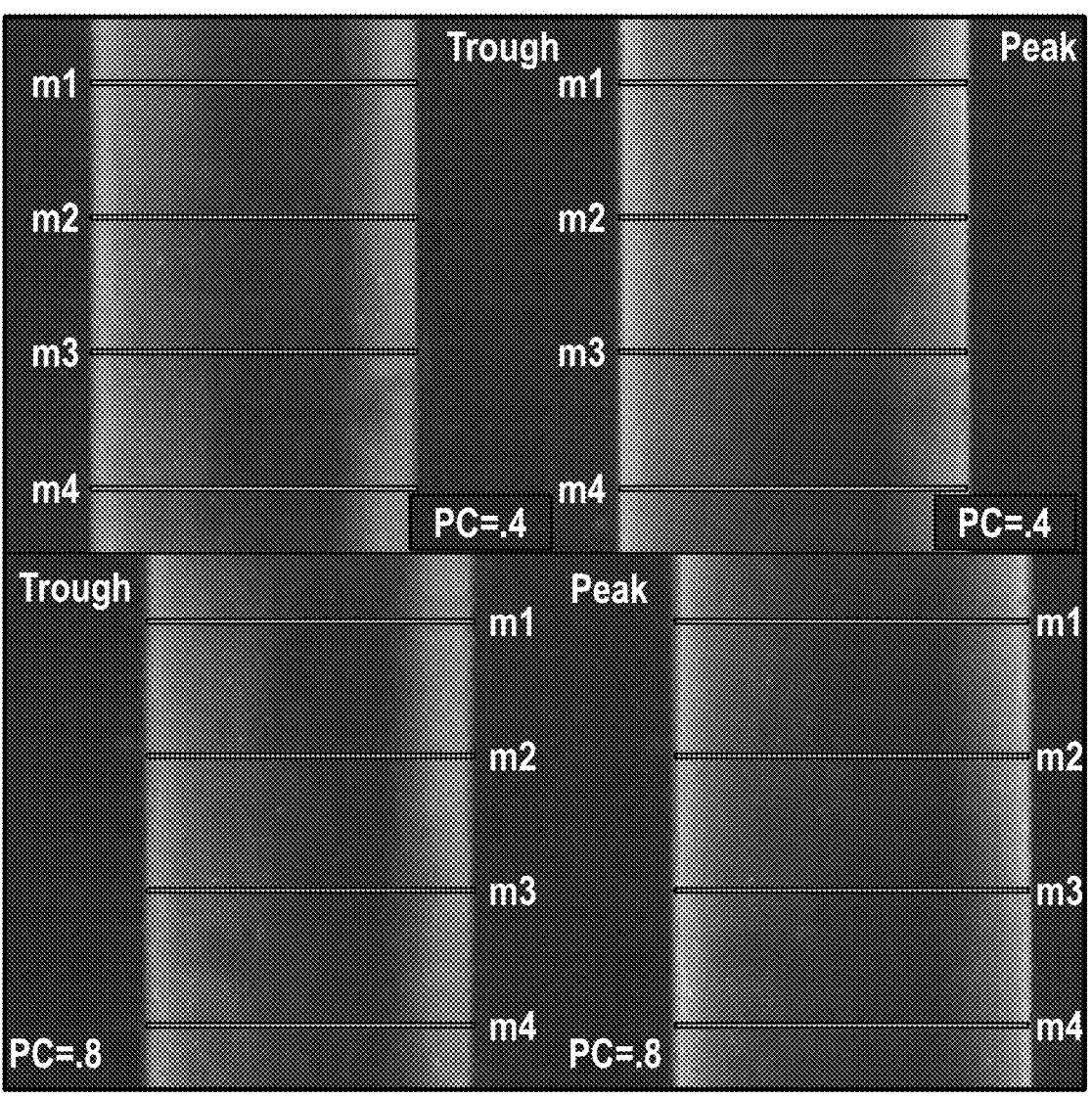
FIG. 8C                    FIG. 8D

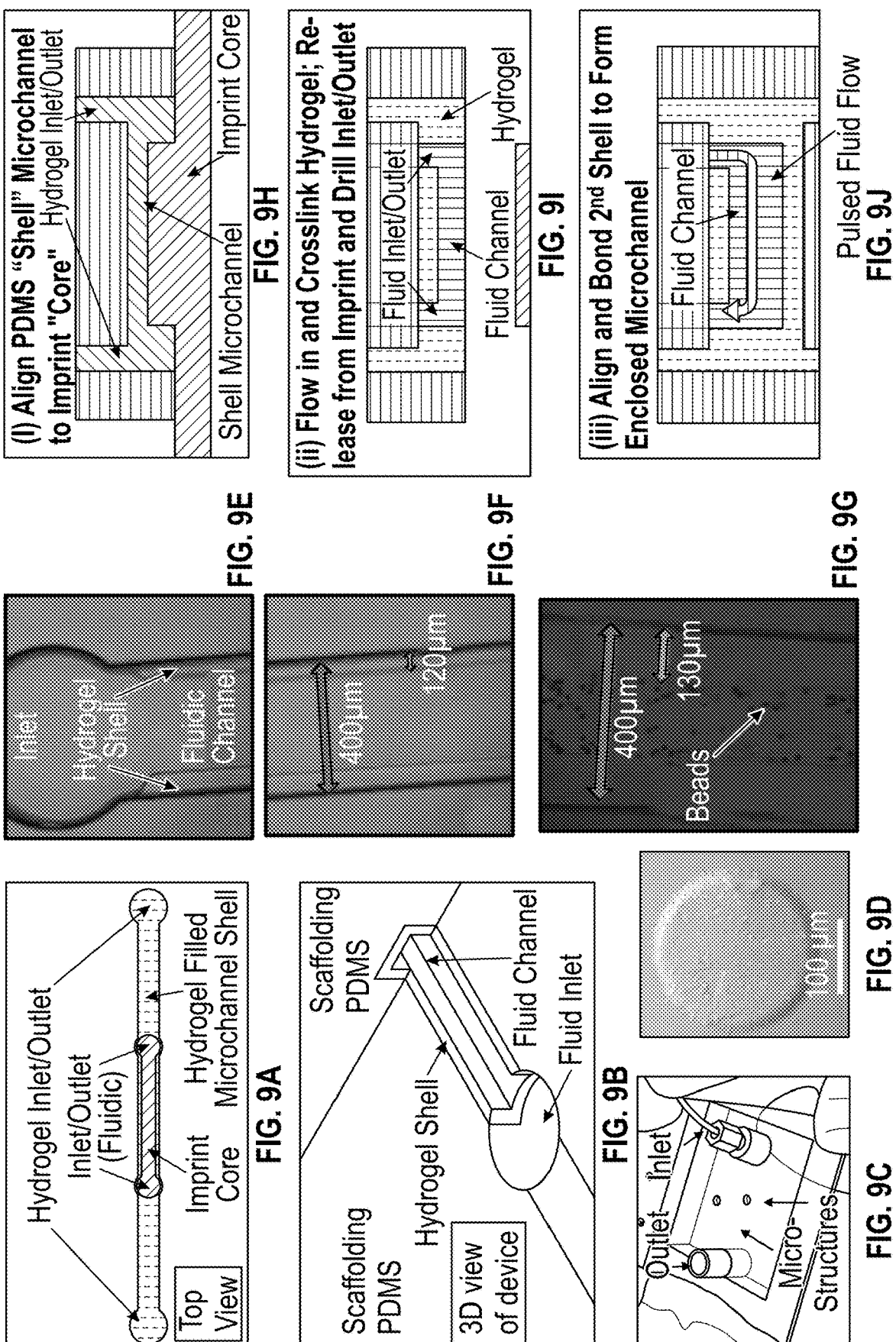

(I) Align PDMS "Shell" Microchannel to Imprint "Core"

Hydrogel Inlet/Outlet

Imprint Core

Shell Microchannel

FIG. 9H

(ii) Flow in and Crosslink Hydrogel; Release from Imprint and Drill Inlet/Outlet Hydrogel Fluid Inlet/Outlet Fluid Channel

FIG. 9I

(iii) Align and Bond 2nd Shell to Form Enclosed Microchannel

Fluid Channel

Fluid Channel

Pulsed Fluid Flow

Inlet

Hydrogel Shell

Fluidic Channel

Beads

Hydrogel Inlet/Outlet

Inlet/Outlet (Fluidic)

Hydrogel Filled Microchannel Shell

Imprint Core

Top View

FIG. 9B

Scaffolding PDMS

Scaffolding PDMS

Hydrogel Shell

Fluid Channel

Fluid Inlet 3D view of device

FIG. 9C

Outlet   Inlet

Micro-Structures

1100
Top View      Cross-section
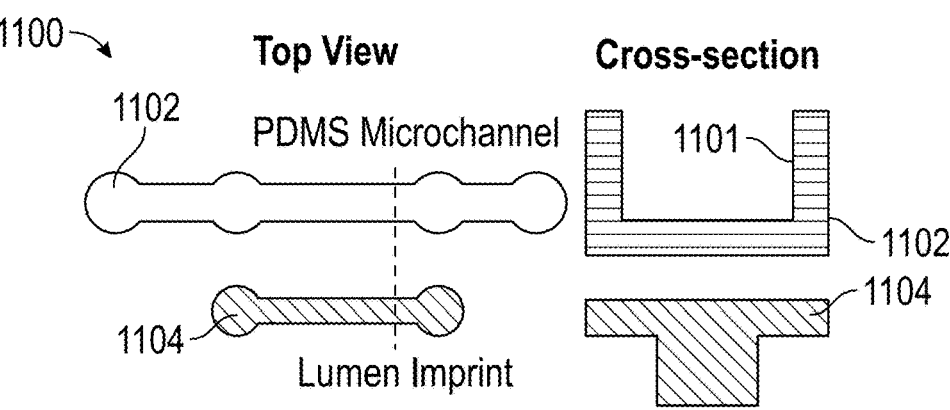
1: The Lumen Imprint is Aligned Within the Microchannel
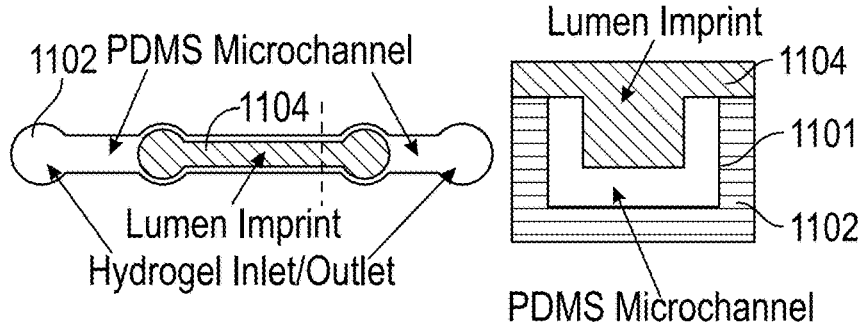
2: Hydrogel is Flown into the Microchannel and Cross-linked
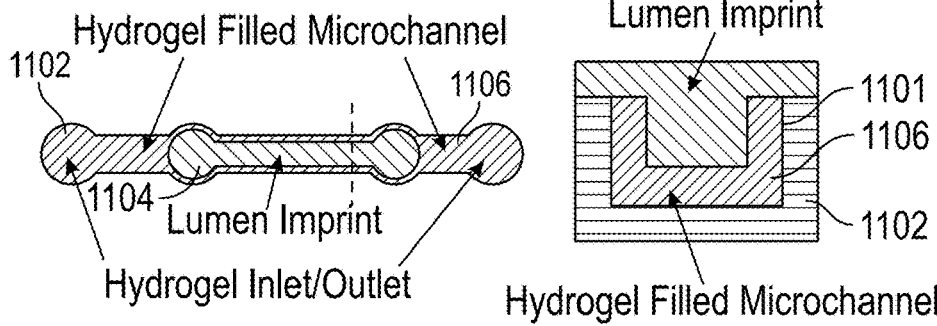
3: Lumen Imprint is Released Leaving a Perfusable Microgel
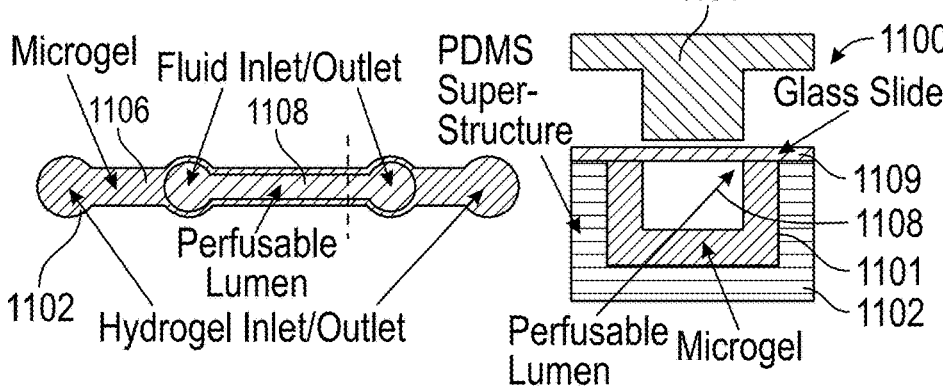
FIG. 11

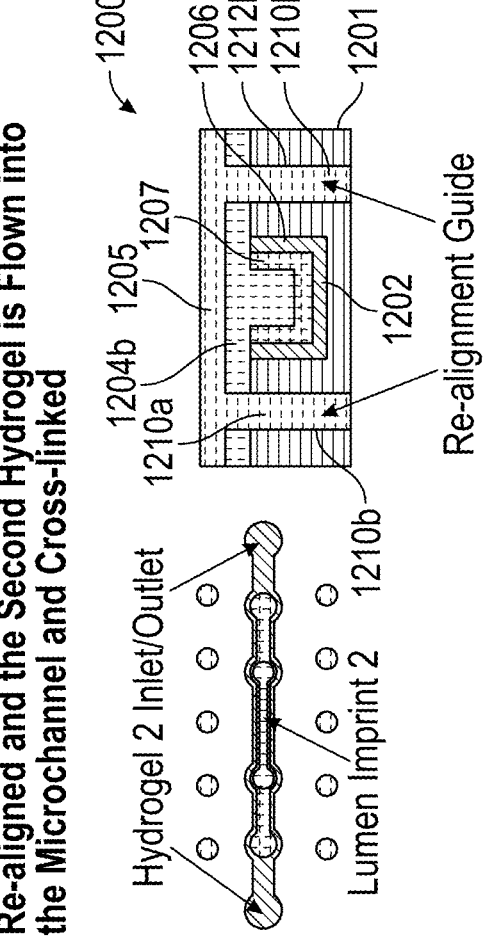
4: Using the Guides the Second Lumen Imprint is Re-aligned and the Second Hydrogel is Flown into the Microchannel and Cross-linked
FIG. 12A1

B
Top View                              Cross-Section
1: Using the Methods from A Realignment Guides for the Second Imprint is Made and the First Imprint is Aligned and Hydrogel is Filled in the Channel
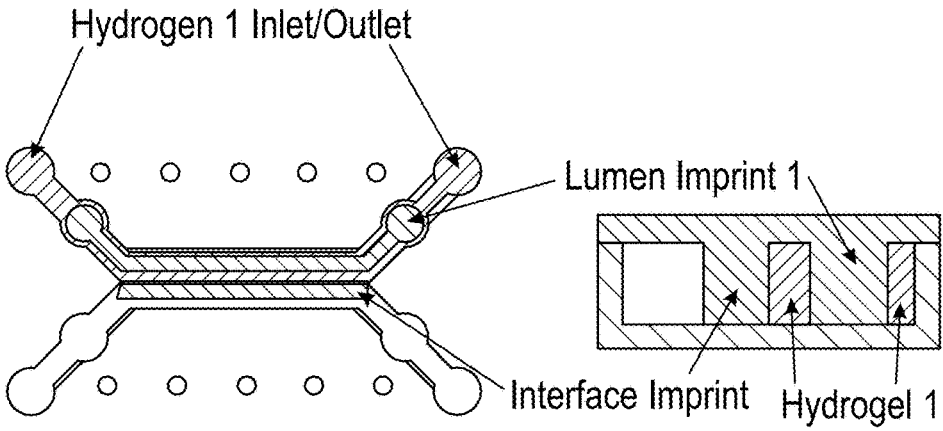
2: Using the Guides the Second Lumen Imprint is Re-aligned
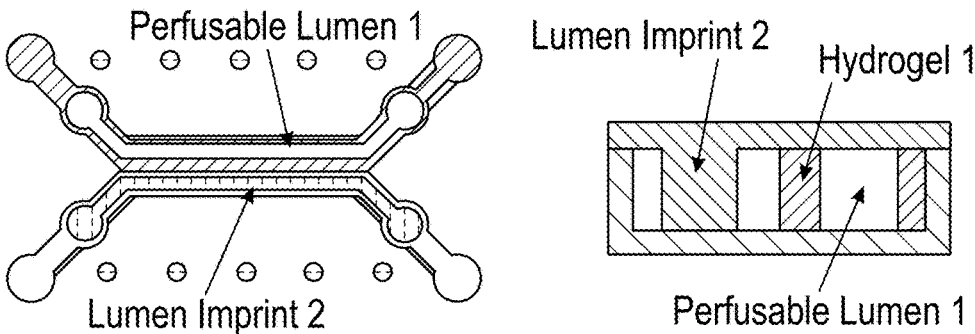
4: The Second Hydrogel is Flown into the Microchannel and Cross-linked Forming a Hydrogel/Hydrogel Interface
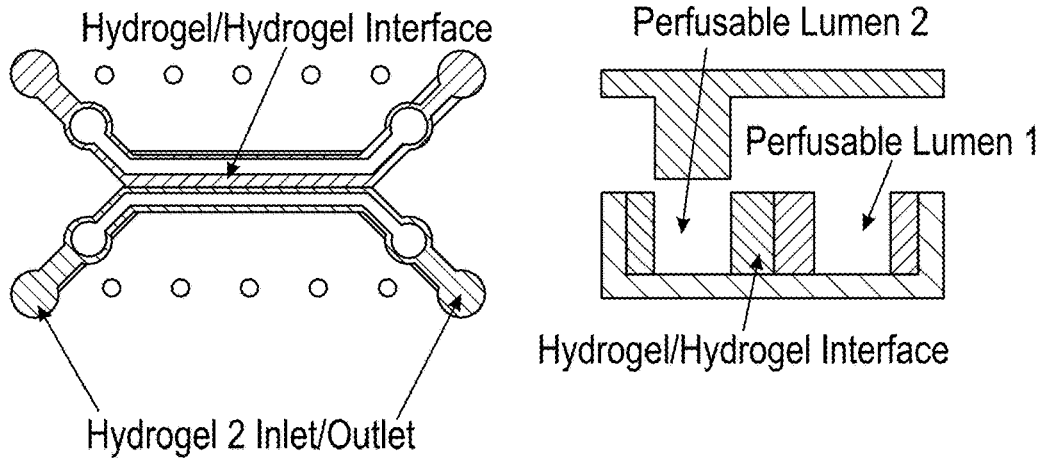
FIG. 12B

PERFUSABLE HYDROGEL MICROCHANNEL SHELL AND METHODS THEREOF

CLAIM OF PRIORITY

This patent application claims the benefit of priority, under 35 U.S.C. Section 119(e), to Nathan Swami U.S. Patent Application Ser. No. 63/092,630, entitled "Microfluidic Imprint Fabrication of Patterned and Perfusable Cell-laden Hydrogels for 3D Culture," filed on Oct. 16, 2020, which is hereby incorporated by reference herein in its entirety.

STATEMENT REGARDING FEDERALLY SPONSORED RESEARCH OR DEVELOPMENT

This invention was made with government support under award number FA2386-21-1-4070 awarded by the Air Force Office of Scientific Research. The government has certain rights in this invention.

BACKGROUND

Microfluidic devices are relatively small devices that can be used to manipulate fluids in small fluidic channels. The size and geometry of the channels and structures of the devices can provide favorable conditions (e.g., Reynolds number) for manipulating fluid flowing through the channels. These conditions can be useful for manipulating cells such as for performing biological experiments or operations on the microfluidic devices. These operations can include cell separation and analysis. In other examples, microfluidic devices can be used to create an in vivo model for one or more components of a human or animal body, such as an in vivo vascular model.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2A illustrates a process flow for fabrication of single lumen structures.

FIG. 3B illustrates a cut away of a multi-biomaterial structure.

FIG. 3C illustrates a brightfield image of a multi-bioma-terial structure.

FIG. 3D illustrates a cut away of a perfusable hydrogel.

FIG. 3E illustrates a brightfield image of a perfusable hydrogel.

FIG. 4A illustrates a schematic showing a process flow for patterning a microgel featuring interfaces between two bio-materials.

FIGS. 5H-5I illustrate images of a hydrogel channel undergoing cyclic stretch.

FIGS. 5J-5K illustrate images of a hydrogel channel experiencing shear stress due to flow rate variations.

FIGS. 5L-5M illustrate images of endothelial cell morphology.

FIGS. 7A-7D illustrate isolated brightfield images of perfused lumen.

FIGS. 8A-8D illustrate isolated brightfield images of perfused lumen.

FIGS. 9A and 9B illustrate a process to fabricate channels in hydrogel.

FIG. 9C illustrates a perspective view of an example microfluidic device.

FIG. 9D illustrates a perspective view of wet alignment (as shown in FIG. 9D).

FIGS. 9E and 9F illustrate example hydrogel channels.

FIG. 9G illustrates fluidic pulsing with sample beads.

FIGS. 9H-9J illustrate a fabrication sequence.

FIG. 11 illustrates a process flow for fabrication of single lumen structures.

FIG. 12A1 illustrate schematics of a process flow for fabricating devices.

FIG. 12B illustrate schematics of a process flow for patterning a microgel.

DETAILED DESCRIPTION

A vast majority of cells in the body lie within 100 micrometers (μm) of patterned and perfusable microvascular systems. Yet, current in vitro tissue models fail to fully recapitulate the biological complexity obtained from spatial cues produced by multiple aligned cell types, as well as the temporal cues obtained from a variety of flow profiles. Such microscale transport cues, which are important for the delivery of nutrients and removal of waste, are not easily captured in 3D cell culture models, thereby limiting both the size and complexity of tissue constructs that can be created, and furthermore, failing to provide the most apt in vitro disease models.

The present disclosure helps to address these issues by using core-shell hydrogel constructs with addressable microfluidic cores that enable perfusion with specific flow profiles, for the purpose of providing temporal cues to the cells patterned in the hydrogel. This model construct can mimic the topology/architecture of microvasculature, which can provide the opportunity to explore, evaluate, and refine the micro-physiological transport features that are a prereq- uisite to accurate modeling of function in vivo. Examples cues include pulsatile flow, modifiable wall compliance, and induced wall shear stress, all of which are required for cell proliferation and tissue growth in more native-like 3D tissue culture systems.

The above discussion is intended to provide an overview of subject matter of the present patent application. It is not intended to provide an exclusive or exhaustive explanation of the invention. The description below is included to provide further information about the present patent appli- cation.

Figures 1A, 1B, 1C:
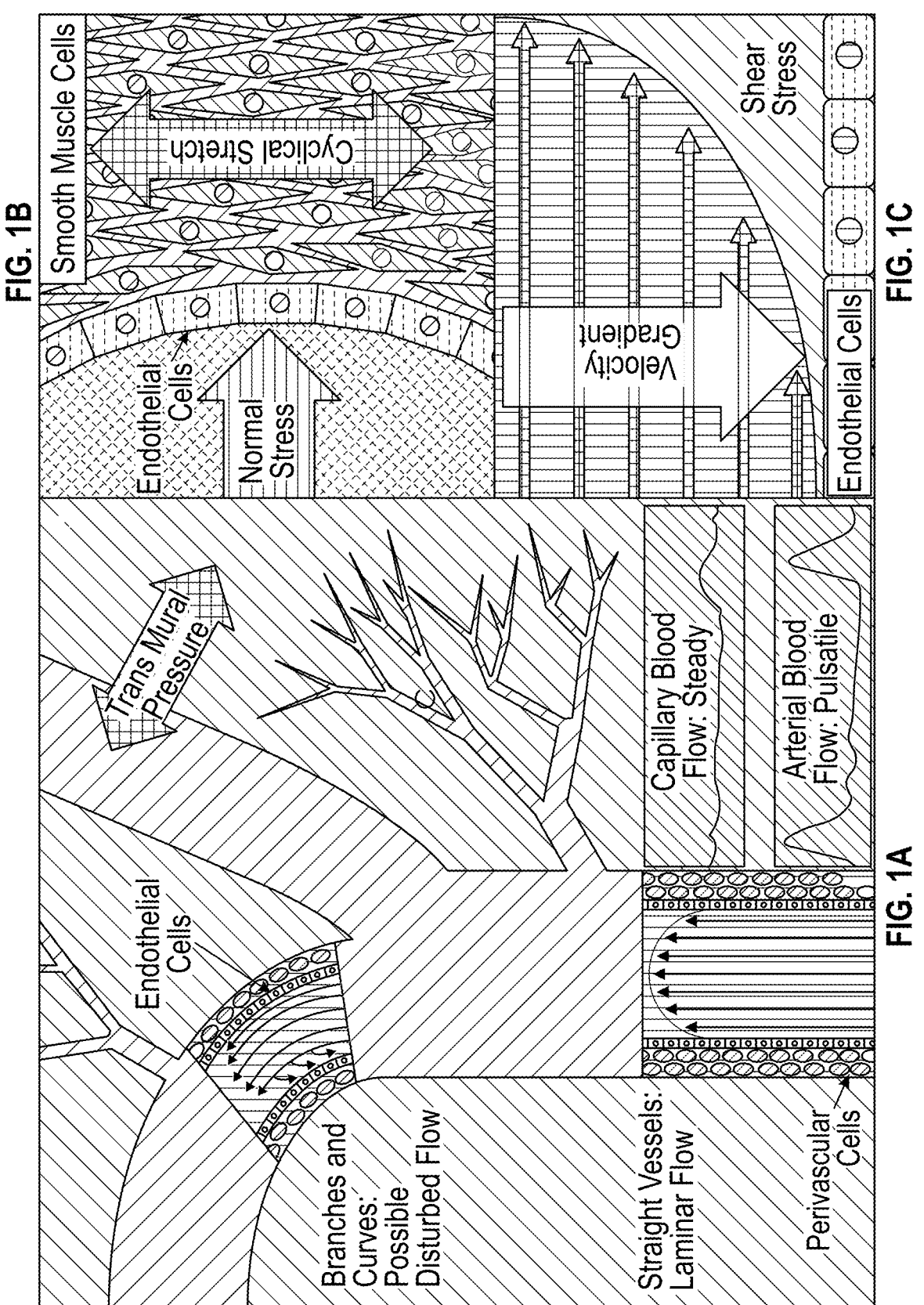
FIG. 1A illustrates an effect of mechanical factors on tissue around vasculature.
FIG. 1B illustrates an effect of mechanical factors on cyclical stretch.
FIG. 1C illustrates an effect of mechanical factors on shear stress incident on endothelial cells.

FIG. 1A illustrates an effect of mechanical factors on tissue around vasculature. FIG. 1B illustrates an effect of mechanical factors on cyclical stretch. FIG. 1C illustrates an effect of mechanical factors on shear stress incident on endothelial cells (ECs). FIGS. 1A-1C are discussed together below.

The development of in vitro tissue models that recapitu- late complex physiological environment and cues present within in vivo tissues is recognized as a desire for bioengi- neering applications, such as drug testing, regenerative medicine, tissue engineering, and disease modelling. Early approaches to reproduce these environments in vitro utilized two-dimensional (2D) cell culture models with engineered interfaces between the different cell types, such as an artificial membrane model, cone and plate model, and the standard trans-well membrane system. While these approaches allow for transport of metabolites between the associated cell types, they do not suppress signaling path- ways associated with intercellular mechano-transduction due to the isolation of neighboring cell types. Additionally, the cells in these models are often placed against materials that are far stiffer than those encountered in vivo, thereby limiting the role of compliance and shear, as well as signals delivered through extracellular matrix interactions.

Hydrogel-based 3D cell culture models can recapitulate these native-like environmental and material cues. However, integration of 3D cell-laden hydrogel cultures with resis- tance vessels (μ100-200 μm) and microvasculature (arteri- oles of 100 μm and capillaries of about 5-10 μm) at physi- ologically relevant scales has remained a challenge. Beyond facilitating nutrient delivery and waste removal, these vessel structures can also shape mass transport in important ways, due to the intimate juxtaposition of the endothelial lining surrounding perivascular cell structure (such as vascular smooth muscle cells), and the adjacent tissues, as shown in FIG. 1A. The conformation of tissue interfaces around the vasculature, in relation to these spatiotemporal cues are significant for angiogenesis, immune response, cell migra- tion, and metastasis. Mechanical cues delivered to the sur- rounding vasculature can profoundly influence cell archi- tecture and function. Their recapitulation relies on the ability to modulate flow conditions within a perfusable lumen or channel.

Across the circulatory system, there are wide variations in diameter of the vessels and the flow rate of blood through them, which can affect the delivered shear stress to the endothelial walls (reported range of 1-6 dynes per centime- ter squared (dynes/cm$^2$) for veins and 10-70 dynes/cm$^2$ for arteries). Perivascular cells, shielded by the endothelium, experience low rates of shear as a result of interstitial flow. Furthermore, pulsatile fluid flow delivered to the relatively elastic arteries, veins and surrounding tissues can result in an increase in lumen diameter over short durations. This results in cyclical stretch, as shown in FIG. 1B, of surrounding tissues influences the alignment of endothelial cells, as shown in FIG. 1C, and perivascular cells, such as smooth muscle cells (SMCs). Hence, perfusion systems to recapitu- late multiscale vascular anatomy of ECs and SMCs, as well as to independently control flow rate, lumen pressures, and temporal flow profiles, to a high degree of spatial resolution are needed. Recreation of perfusable lumens of 3D hydrogel biomaterials, along with the associated multicellular topolo- gies at physiological scales, has proven difficult. This limits the ability to recapitulate tissue-to-tissue interactions as found in natural tissues, as well as to deliver physiological scale flow rates and pressures to 3D cell-laden hydrogels.

Microfluidic systems based on poly-di-methyl siloxane (PDMS) can offer a diverse range of methods for precise flow and pressure control, as well as for recapitulating complex physiological flow states. This platform can benefit from ease of integration with fluidic control systems, thereby allowing for a high level of spatial or temporal control of perfusion parameters. This disclosure discusses a strategy for the fabrication and use of micropatterned single or multi-shell hydrogel structures (microgels) that can func- tion as perfusable lumens that are aligned within a PDMS superstructure for enabling their facile integration with fluidic control systems. In this manner, spatially and tem- porally controlled fluidic cues can be delivered to cells and tissues during 3D culture. Such a fabrication method can combine microfluidic and imprint lithography methods to pattern these microgels with high-resolution lumens. Imprint lithography and micro-molding can be capable of replicating micron to submicron-scale grooves, channels, or textures within biomaterials. However, since hydrogel patterning occurs over the imprinted surface, a large region of residual biomaterial can be situated away from the patterned region. Conversely, microfluidic patterning offers a method to sig- nificantly restrict the bounds of the hydrogel structure, but it is often limited in its ability to pattern negative spaces internal to the gel structure, such as for adding grooves or channels. This disclosure discusses a methodology of micro- fluidic imprint lithography (MIL) that utilizes the high tolerance and reversible nature of the bond alignment pro- cess to lithographically position imprints within a microflu- idic device to enable the sequential filling and patterning of lumens of microgels, thereby leveraging the benefits of both parent processes. PDMS microfluidic channels, which can be fabricated at high-resolution by micro-molding from lithographically patterned SU8 resists can be used to bound the outer dimension of the microgel lumen, while other PDMS imprint structures can shape the inner dimension of the microgel lumen, thereby creating grooves, channels, or internal patterns. Once aligned and reversibly bonded together, the outer microchannel and imprint structure can form a sealed cavity that tightly confines the extent of any resulting hydrogel structure, thereby limiting any residual layer of hydrogel outside of the patterned area. This, in conjunction with high-resolution lithographic alignment, can allow for each subsequently patterned structure to be aligned independent of the previously formed structure, thereby enabling the fabrication of nested, freestanding, or interfaced microgels.

Following patterning, the resulting microgel structure can either be released from the microfluidic channel to create stand-alone structures or can remain inside the scaffolding provided by the PDMS superstructure, so that each lumen can be individually addressed by fluidic cues. The PDMS superstructure can also act to reinforce the microgel lumen structure to allow for perfusion to deliver chemical cues at physiologically relevant flow rates and pressures. Fluidic interfacing to the single or multiple shell microgel lumen structures can be validated by presenting the delivery of physiologically relevant mechanical cues for recapitulating shear stress and cyclical stretch factors to cells within the structure. In this manner, not only do these methods produce the desired bio-functionality and topology of micro-vasculatures, but can also create the features of relevance to biological flow, such as the ability for pulsation, modifiable wall compliance, and induced wall shear stress, which can eventually create the cues to recapitulate micro-vasculature growth in patterned and perfusable 3D culture systems.

Figures 2B, 2C, 2D, 2E, 2F, 2G:
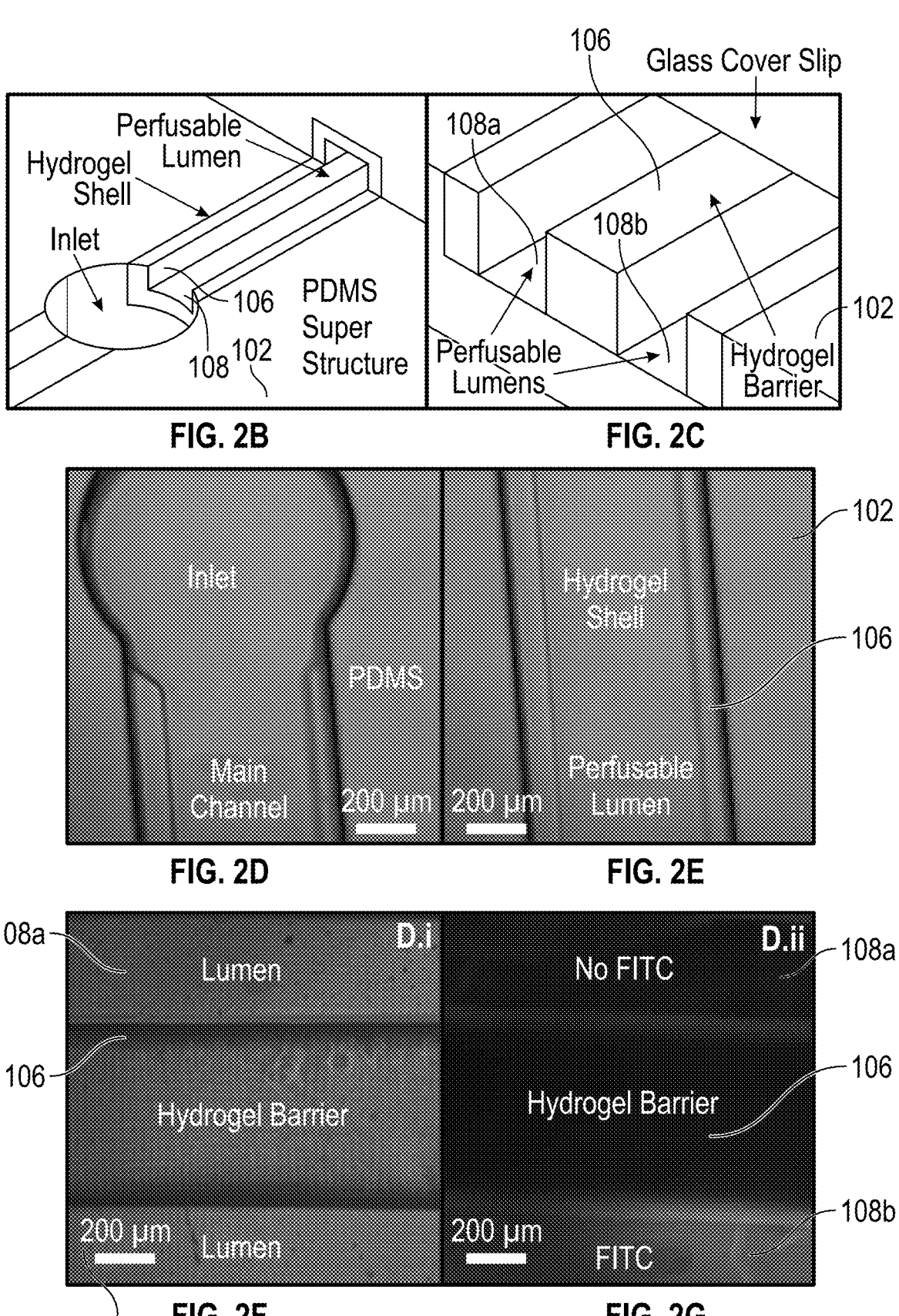
FIGS. 2B-2C illustrate cut away diagrams of the single and double lumen co-culture device.
FIGS. 2D-2E show images of the fluidic inlet and main channel for the single lumen co-culture device.
FIGS. 2F-2G show bright field images of a hydrogel structure and a florescent image of hydrogel barrier.

FIG. 2A illustrates a process flow for fabrication of single lumen structures. FIGS. 2B-2C illustrate cut away diagrams of the single and double lumen co-culture device. FIGS. 2D-2E show images of the fluidic inlet and main channel for the single lumen co-culture device. FIGS. 2F-2G illustrate a bright field Image of 500 μm hydrogel structure flanked by two 500 μm individually addressable lumens and a florescent image of hydrogel barrier interceding lumens filled with unlabeled and Fluorescein isothiocyanate (FITC) labelled Poly-L-Lysine using addressable fluid channels. FIGS. 2A-2G are discussed together below.

To fabricate a perfusable micron-scale hydrogel structure (microgel) integrated within a PDMS superstructure 102, a combined microfluidic patterning and aligned imprinting process can be utilized. A microfluidic imprint lithography (MIL) method can use a PDMS core imprint 104 component to define open areas forming a perfusable lumen of the microgel, as shown in FIG. 2A. The core imprint 104 can then be aligned to a shell microchannel 101 using a reversible bond alignment process. To limit contact between the PDMS chip and the bond chuck during alignment by wedge error correction (WEC), a metal frame can be used to parallelize the two pieces over a fixed distance. The core imprint component can then be inserted into the shell microchannel 101, which can define the microgel's outer diameter and also act as structural reinforcement for perfusion. The lumen imprint 104 can be reversibly bonded to the channel 101 under external pressure to create an enclosed microchannel that defines the microgel dimensions. Hydrogel (such as a microgel made of gelatin methacrylate or GELMA) can be filled into the microchannel through a syringe pump and then cured using the UV crosslinking method to form the microgel 106. To improve adhesion of the gel within the microchannel, a methacrylate silane layer can be deposited on the shell microchannel 101 prior to alignment. The core imprint 104 can then be then de-bonded to define the lumen of the hydrogel lined microfluidic channel. To facilitate a clean release and limit damage to the microgel pattern, the PDMS core imprint 104 can be treated with an anti-stiction layer (e.g., 1% BSA or Bovine Serum Albumin). After release, the channel 101 can be sealed to form a perfusable microgel embedded in a PDMS superstructure defining a lumen or channel 108. Though a lumen is typically enclosed, the term lumen is used herein as being at least a portion of a channel, lumen, passageway, or the like.

Rigidity of the PDMS components can be tailored according to their function, such as by varying the base to curing agent ratio and the curing temperature, with high rigidity components used for the imprint structure and high compliance components used for application requiring cyclical stretch.

Single-Imprint Lumen Structures

The versatility of the microfluidic imprint lithography method can be used to create microfluidic hydrogel lumens by constructing patterned structures of single microgel lumens for potential application within 3D co-culture systems. One example of an architecture can include a single hydrogel biomaterial using only a single imprint step. As shown in FIGS. 2B-2C, a structure designed for possible coculture application with endothelial cells (ECs) can include a straight perfusable lumen 108 surrounded by the physiologically relevant hydrogel shell 106, which can include ECs cultured on the inside surface of the lumen, while the hydrogel can be laden with perivascular cells or other cells of interest (as discussed in further detail below). A thickness of the hydrogel shell 106 can be designed based on typical mass transport distances in vivo, of 100-200 μm away from the vessel. This perfusable microgel can reinforced by a PDMS superstructure 102, with a rigidity that can be tuned to allow for appropriate cyclical stretch under pulsed physiological scale fluid flow.

Using the single lumen design of FIGS. 2B-2D, the dimensions of a rat carotid artery can be used as a model. To replicate this pattern a 1 cm long straight lumen imprint with a height of 250 μm and a width of 480 μm can be aligned within a 1.5 centimeter (cm) long and 375 μm high by 750 μm wide straight channel. This can result in a hydrogel shell (130 μm thickness) around a 1 cm long perfusable lumen, with dimensions identical to the insert. Once formed, this device can be aligned and bonded with an identical device to create an enclosed 500 μm by 500 μm square lumen. It can also be bonded to a glass cover slip forming a half lumen, such as for enabling facile imaging using inverted microscopy. The thickness of the biomaterial shell around perfusable lumen can be significantly limited to ensure that the transport of chemical cues across the cultured EC layer resemble in vivo length scales.

Another example of a single imprint architecture shown in FIGS. 2C and 2F-2H is a microgel containing two individually addressable perfusion channels 108a and 108b, with an interceding hydrogel structure (e.g., 500 μm wide), as would be used for creating chemotactic gradients for cells laden in the hydrogel. For this structure, 500 μm high by 500 μm wide lumens can be formed simultaneously within a microgel 106 that is integrated in a PDMS channel (e.g., 2 mm wide by 500 μm high) 102. These parallel channels 108a and 108b can maintain their 500 μm separation over a length of 1 cm.

The two lumens 108a and 108b can be fluidically addressable, since the two lumens branch away from each other through individual channels outside of this overlap region to independent sets of inlets and outlets. This ability to address each channel is shown in FIGS. 2D-2E wherein one channel can be filled with PBS (phosphate buffered saline) containing 1 mg/mL FITC labelled Poly-L-lysine and the adjoining channel can be filled with the respective un-labelled fluid. By using the MIL method, since the patterned imprint component is responsible for defining the configuration of the liquid gel interface, the width of the perfusable channels and the width of the gel separating the adjoining channels can be tailored over a relatively large spatial extent of active region. For instance, the lumen width can be varied to create a gradation in shear stress along the channel length or the hydrogel width can be modulated to alter the diffusional profile of species through the hydrogel.

Design of Multiple-Imprint Biomaterial Structures

Figure 3A:
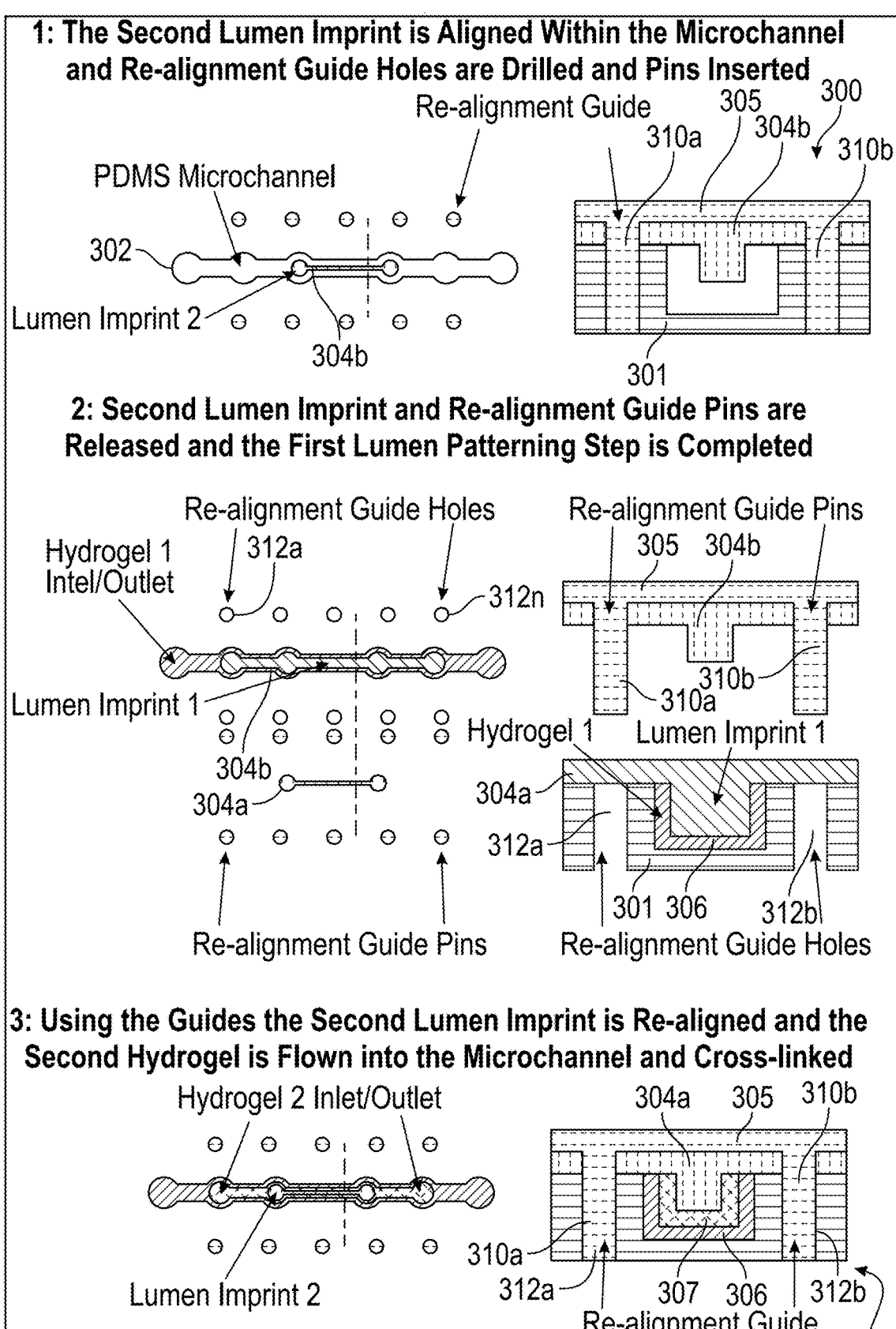
FIG. 3A illustrates a process flow for fabricating devices including multiple imprints.

FIG. 3A illustrates a process flow for fabricating devices requiring multiple imprints based on 3D printed constructs for alignment of hydrogels over multiple layers without desiccation. FIG. 3B illustrates a cut away of a multi-biomaterial structure and FIG. 3D illustrates a brightfield image of a multi-biomaterial structure featuring two individually patterned hydrogels separated by a lumen. Beads can be added to the hydrogel that is patterned first to improve image definition. FIG. 3C illustrates a cut away of a perfusable hydrogel and FIG. 3E illustrates a brightfield image of a perfusable hydrogel featuring two individually patterned hydrogel shells around a single lumen. Beads can be added to the hydrogel that is patterned first to demonstrate layer definition.

To integrate multiple types of patterned biomaterial structures within the perfusable microgel, the above-discussed process can be to be repeated with a second imprint component to form an assembly 300 (e.g., 300a or 300b). However, to avoid desiccation of the hydrogel, the time-consuming interlayer alignment steps can be performed on the mask aligner prior to introduction of the hydrogel material. Hence, after the first hydrogel pattern is formed, a method to rapidly re-align the previously aligned core and shell components can be used to pattern subsequent hydrogel structures, as shown in FIG. 3A. For this purpose, a second imprint component 304b can be first aligned to a microchannel 301 by the previously outlined methods. After the reversible bonding step, re-alignment guide holes 312a and 312b (or 312a-312n, such that any number of guide holes can be used) can be drilled through two aligned components in a configuration set by a 3D printed holder, such as by using a biopsy punch. The aligned components can then be mounted on a 3D printed scaffold 305 using pins 310a and 310b (or 310a-310n, such that any number of pins can be used) that correspond to the layout of drilled alignment holes 312a and 312b, respectively. The channel can then be released, leaving the imprint core 304b still mounted on the scaffold 305. The first microgel patterning step can then be completed as outlined above, such as using a first imprint core 304a to for the first microgel 306. After a first microgel 306 has been formed, the channel 301 can then be rapidly re-aligned to the second imprint core 304b by mounting it back on the scaffold 305 using the pins 310a and 310b and alignment holes 312a and 312b. A second biomaterial can then be filled into the device and crosslinked to form a second microgel 307 (or layer hydrogel layer) to form multi-material microgel structure, as shown in FIG. 3A and FIGS. 3B and 3C.

Patterning of Multi-Biomaterial Lumen Structures

To highlight this ability to rapidly re-align subsequent imprint cores after an initial hydrogel patterning step, perfusable microgels featuring multiple types of individually patterned biomaterial structures can be created. These structures can be used to create engineered liquid tissue biomaterials and tissue-tissue interfaces of relevance to co-culture systems. For example, FIG. 3C-3E shows a modification of the single channel co-culture chip described above. In this example, a second lumen imprint with smaller dimensions is aligned within the lumen formed during the initial patterning step, as discussed above. After alignment, a second hydrogel can be introduced to form an inner shell. The resulting perfusable hydrogel structure features a single (for example, 500 μm wide by 300 μm high) lumen surrounded on three sides by two nested hydrogel layers of 125 μm thickness. For application to co-culture systems, each of these hydrogel layers 306 and 307 can be laden with a different set of target cells. Other nested gel interfaces have been created in the past; however in such creations an outer diameter of the gel layer is not confined, which can limit perfusion due to significant differences in scale between the two tissue structures. On the other hand, the structures of the present disclosure (e.g., assembly 300) can replicate a size scale over which mass transport can occur from vessels to the surrounding tissue in vivo, thereby allowing for tissue-to-tissue interactions that lead to the formation and preservation of chemical gradients across tissues or for variations in nutrient, dissolved oxygen, or other chemical cue levels. That is, the assembly 300 (and other similar assemblies) can be used for more accurate in vivo models.

Design of Multi-Hydrogel Interfacial Structures

Figure 4B:
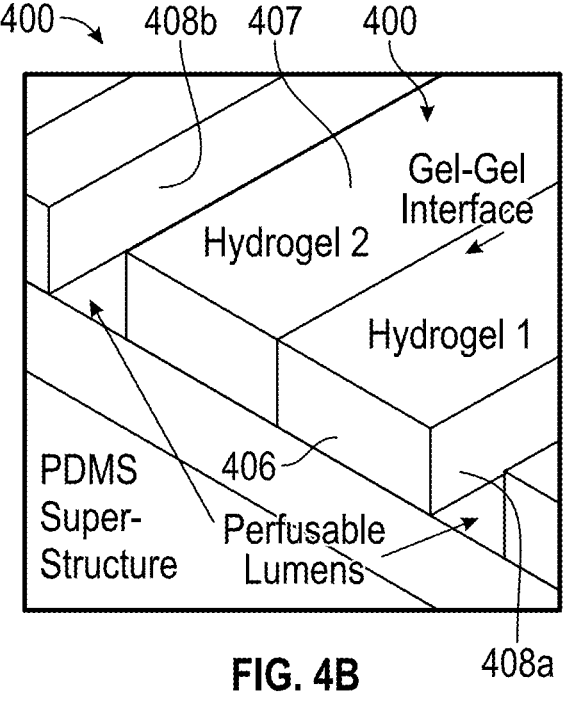
FIG. 4B illustrates a cut away 3D model of a final device structure.
Figure 4C:
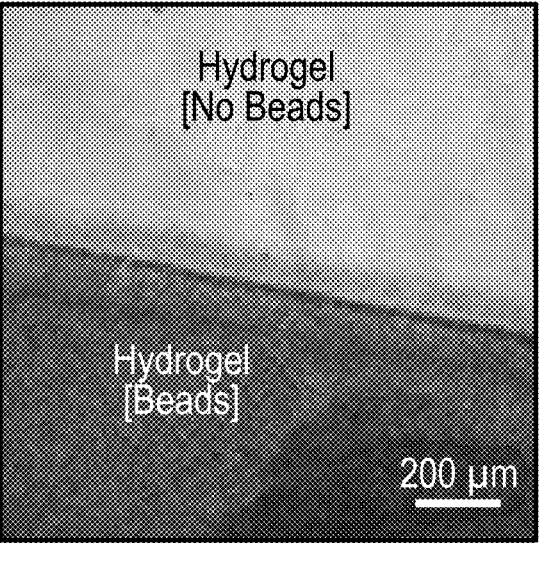
FIG. 4C illustrates a bright field images of a device.
Figure 4D:
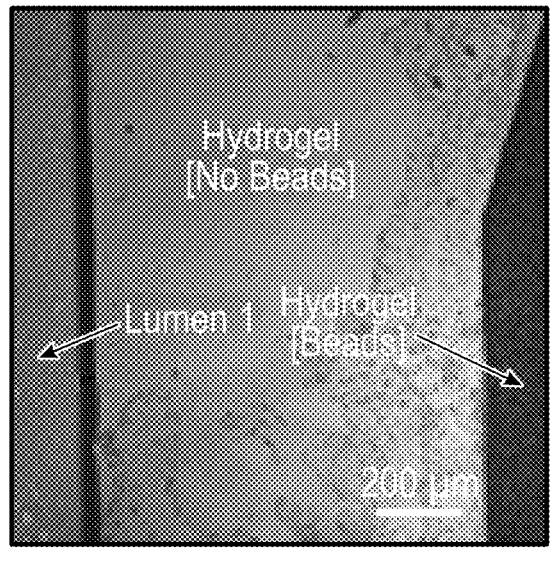
FIG. 4D illustrates a bright field images of a device.
Figure 4E:
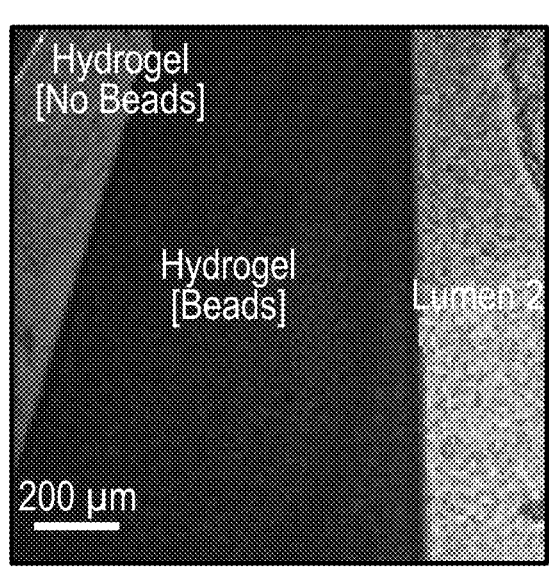
FIG. 4E illustrates a bright field images of a device.

FIG. 4A illustrates a schematic showing a process flow for patterning a microgel featuring interfaces between two biomaterials. FIG. 4B illustrates a cut away 3D model of a final device structure. FIGS. 4C-4E illustrate bright field images of a device featuring two individually patterned hydrogel structures. These structures are patterned to form a gel-gel interface between them, with ability to modulate length of the interface. The entire structure can be flanked on either side by a perfusable 500 μm lumen. Beads are added to the initially patterned hydrogel structure for enhancing image definition.

Through multiple imprint steps, it is possible to utilize the MTh process for the fabrication of complex 3D interfaces between perfusable bio-functional hydrogel structures, such as those of different hydrogel materials or those laden with different cell types. While open space within the microgel formed during the imprint step has been used in the prior section as a perfusable lumen, it can also be used to pattern gel-to-gel interfaces by filling-in the open space with another hydrogel. In these applications, a first imprint 404a can be used to define a lumen 408a and the hydrogel barrier 406, which can function as one side of the gel-to-gel interface. Such imprints can be designed with a feature 414 (e.g., wall, divider, or the like), which after appropriate alignment, can limit hydrogel flow to a portion of the shell microchannel 401, thereby patterning the spatial extent of the resulting structure. A second hydrogel precursor can then be filled into the portion of the microchannel and crosslinked. During this step a second imprint 404b may be aligned by the process outlined above within this open space, forming a perfusable channel 408b within the second hydrogel structure 407, as well as the gel-to-gel interface 416 (as shown in FIG. 4A).

Patterning of Multi-Hydrogel Interfacial Structures

To highlight this feature, a, for example, 2 mm wide composite structure can include two individually patterned hydrogel biomaterials, with an engineered interface between them. This structure can positioned between two parallel individually addressable perfusable (e.g., 500 μm) wide microchannels (as shown in FIG. 4B), similar to the single material iteration described above. The overall combined width of the hydrogel structure can remain consistent over the 7.5 mm length over which the parallel channels interact. To demonstrate the versatility possible by this design, FIGS. 4D-4E show that the position of the interface between the two gels can be varied, as may be required for a 3D co-culture system that allows for monitoring of the interactions between two types of cells embedded in the respective hydrogels. Additionally, since perfusable channels can be formed, nutrients can be delivered to the cells in each hydrogel. This can allow for formation of gradients of analytes and drugs to be tested. Other methods to obtain gel to gel interfaces within microfluidic channels rely on surface tension or hydrodynamic forces to pattern the interface. Hence, they can only maintain this interface over a limited length (10-100 μm scale), while not allowing for a high degree of variation in the architecture of the patterned gel-to-gel or gel-to-liquid interface, or their feature sizes are at a millimeter size scale. In the present disclosure, on the other hand, since the dimensions of both the lumen and the interface are defined by the micropatterned insert, a far wider variation in architecture is possible.

Validation of Cyclic Stretch and Shear Stress Cues in Perfusable Microgels

Figure 5A:
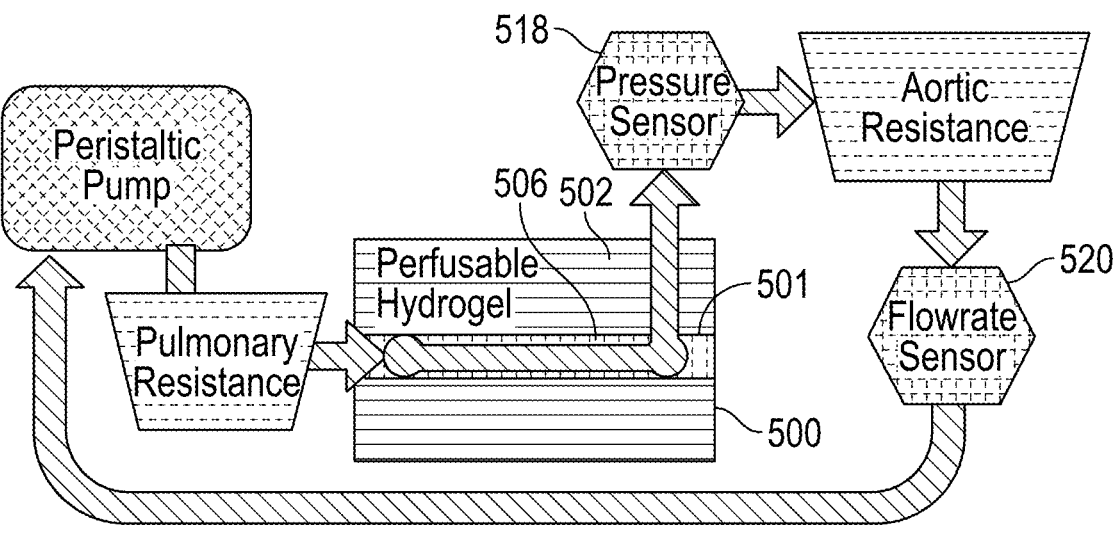
FIG. 5A illustrates a circuit model.
Figure 5B:
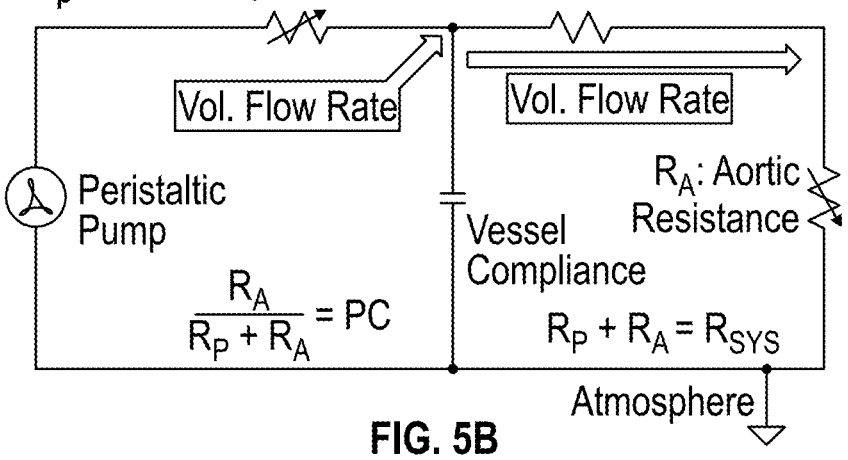
FIG. 5B illustrates a schematic of fluidics for perfusion of hydrogel channel.

FIG. 5A illustrates a circuit model and FIG. 5B illustrates a schematic of fluidics for perfusion of hydrogel channel. A net system resistance (RSYS) and pressure correction factor (PC) determined by pulmonary (RP), and aortic (RA) resistance elements can be tuned to independently set a flow rate and lumen pressure in a channel 501 of a system or device 500 for a range of cell models (as shown in FIGS. 5E-F). The system 500 can be similar to any of the devices or systems discussed above or below.

Figure 5C:
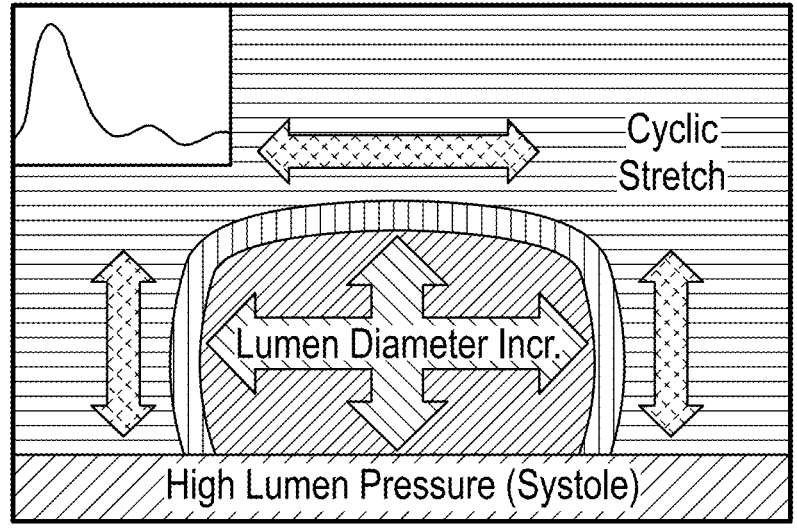
FIG. 5C illustrates a schematic of a system undergoing cyclic stretch.
Figures 5D, 5E, 5F, 5G:
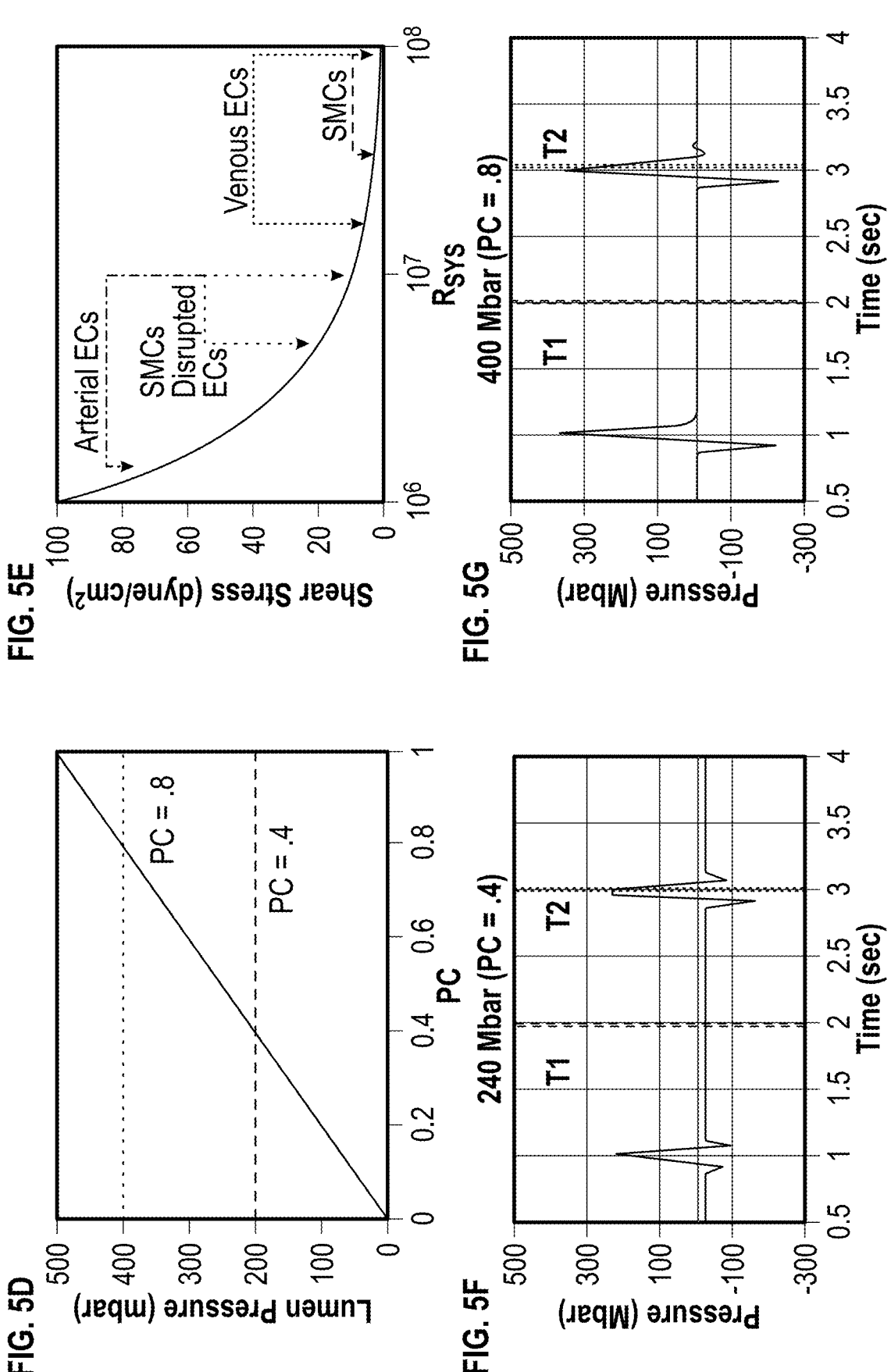
FIGS. 5D-5E illustrate graphs of effects on a system.
FIGS. 5F-5G illustrate graphs of effects on a system.

Due to pressure increase, lumen diameter expands exerting cyclic stretch (as shown in FIG. 5C). The effect of two different pressure pulses from initial state (T1=2 s) to final state (T2=3 s) of 240 mbar (as shown in FIG. 5F) and 400 Mbar (as shown in FIG. 5G) can cause cyclic stretch levels of 5.9% (as shown in FIG. 5H) and 11% (as shown in FIG. 5I). Also, shear stress due to flow rate variations (shown in FIG. 5J vs. FIG. 5K) can alter endothelial cell morphology to cause alignment along flow (as shown in FIG. 5L vs. FIG. 5M).

Mechanical factors associated with pressure driven blood flow, such as wall shear stress and cyclic stretch, can vary widely throughout cardiovascular systems and can have profound influence on cellular architecture and function of tissues surrounding blood vessels. Differences in vessel lumen diameter, blood flow rates, and degree of exposure to blood flow can influence shear stress delivered to surrounding cells. For endothelial cells (ECs), which can be directly exposed to blood flow, shear stress can range from 1-6 dynes/cm$^2$ for veins and 10-70 dynes/cm$^2$ for arteries. On the other hand, smooth muscle cells (SMCs) within healthy vasculature can experience limited shear stress levels due to interstitial flow (e.g., 1-3 dynes/cm$^2$). However, in circumstances of endothelium disruption, SMCs can experience higher shear stress (e.g., 10-20 dynes/cm$^2$). Furthermore, the pulsatile blood flow profile driven by the heart to large diameter vessels, such as arteries and veins, can cause fluctuations in lumen diameter that results in cyclical stretch of surrounding tissues. Shear stress and cyclic stretch can act in tandem to align endothelial and perivascular cell configurations. Given a wide range of physiological effects caused by shear stress and cyclic stretch to vasculature cells (SMCs and ECs), tailoring of flow states to maintaining an adequate perfusion level and facilitating mass transport is desired, so that an in vitro model can replicate a relevant homeostasis or disease state under investigation.

Due to the wide-ranging magnitude and temporal profiles in volumetric flow rate and lumen gauge pressure of physiological blood flow, recapitulation of the associated mechanical factors is challenging to achieve. As such, full recapitulation within perfusable hydrogel-based 3D culture environments is yet to be demonstrated, due to the inability of microgel structures to withstand the required pressures and flow rates. Since the patterned microgels in this disclosure are integrated within a PDMS superstructure 502 for the purposes of bounding, supporting and enabling fluidic interfacing of the embedded microgel, the application of this perfusable microgel platform for delivery of biomimetic mechanical factors under fluid flow is considered.

Shear stress in microfluidic culture is usually modulated by the flow rate and dimensions of the device, while cyclic stretch is determined by the gauge pressure and the Young's modulus of the materials in the device. Facile control of shear stress in the channel can be achieved by altering flow rates, but a similar method to independently control cyclic stretch through delivered fluid flow is not possible. Typically, cyclic stretch is controlled by varying external air pressure and internal fluid pressure over a flexible membrane or by stretching the channel using a specialized external mechanical stage, but this limits the stretch to a single direction and it is often localized over only a limited region of the channel. The devices and methods of the present application address this issue, at least in part, by altering the level of cyclic stretch independent of the flow rate, by utilizing a PDMS superstructure of high compliance (curing agent ratio of 1 to 20) to set the Young's modulus of the device material, while tuning input and output resistors from the microgel to vary the peak value of a pulsed pressure source, resulting in an increase in lumen diameter, as is depicted in FIG. 5C. Per the device schematic in FIG. 5A and the equivalent fluidic circuit in FIG. 5B, the input pulmonary (RP) and output aortic resistors (RA) to the perfusable hydrogel channel device are set based on tubing length, so that this net system resistance (Rsys≈SRP+RA) can be used to fix flow rate and the resulting shear stress, while the ratio of the length of the aortic element to the combined length of aortic and pulmonary elements is used to vary the pressure correction (PC) factor to alter the pressure pulse. In this manner, the effects of cyclical stretch on the hydrogel lumen can be explored, while validating shear stress-induced cues based on alignment of endothelial cell morphology along the flow direction in the perfusable hydrogel channel. By carefully choosing RP and RA, the values of PC and Rsys can be set independent of each other for precise tuning of the flow rate and pressure within the lumen (shown in FIGS. 5D-5E), thereby ensuring a relatively uniform gauge pressure and cyclical stretch along the length of the perfusable channel.

As an example of flow tuning, a 1 cm long, 250 µm high, and 480 µm wide perfusable hydrogel lumen structure comprised of a 10% gelatin hydrogel (enzymatically cross-linked by microbial transglutaminase or mTG) can be used and can be embedded in a 375 µm high by 750 µm wide microgel structure. An inline pressure sensor 518 can be used to determine that PC values of 0.8 and 0.4 result in pressure pulses of 400 millibar (mbar) and 240 mbar, respectively (as shown in FIG. 5F-5G). The resulting increase in lumen diameter due to cyclic stretch from initial state (T1=2 s) to final state (T2=3 s), under gauge pressures of 240 mbar and 400 mbar, can be measured by microscopy as: 5.9% and 11%, respectively (as shown in FIG. 5H and 5I). This is in line with physiological expectations, where cyclical stretch levels range between 5% and 10%, respectively. Based on the dimensions of the lumen, viscosity of the perfused media (which are set for a particular application), and the range of delivered flow rates (such as determined by an inline flowrate sensor 520), several ranges of shear stress can be delivered within the above device for various SMC and EC models (as shown in FIGS. 5D and 5E).

Table 1 shows resistance values (Rsys, RA, and RP) required to deliver pulsed physiological flow rates for a range of EC and SMC culture models for a 500 mbar applied pressure pulse. For visualization, two states of low and high shear stress are shown using beads in the perfusable hydrogel channel (as shown in FIGS. 5J and 5K) and the effect of the shear stress cues on endothelial cell morphology in the channel is shown in FIG. 5L (static culture) versus FIG. 5M where a dynamic culture at 600 microliters per minute (μL/min) is shown. Hence, through embedding the perfusable microgel in a compliant PDMS superstructure with a curing ratio that is adjusted to resemble the stiffness of typical tissues (~0.84 MPa), the microgel channel can undergo cyclic stretch (expand and return to its original state) at biomimetic levels upon being pressurized under fluid flow and can exhibit shear stress under the same flow rate cues.

Table 1 below shows tuning resistor values (Rsys, RA and RP) to modulate cell model specific wall shear and cyclical stretch (Note that RP=RSYS−RA).

| Cell Model | Wall Shear Stress (dynes/cm$^2$) | $R_{SYS}$ ($10^7 \cdot$ Pa $\cdot$ S/Cm$^3$) | $R_A$: PC = .8 ($10^7 \cdot$ Pa $\cdot$ S/Cm3) | $R_A$: PC = .4 ($10^7 \cdot$ Pa $\cdot$ S/Cm3) |
|---|---|---|---|---|
| SMCs | 1.0-3.0 | 10.0-3.34 | 8.0-2.67 | 4.0-1.33 |
| SMCs (Disrupted ECs) | 10.0-20.0 | 1.01-.5 | .804-.4 | .402-.2 |
| ECs Venous | 1.0-6.0 | 10.0-1.67 | 8.0-1.33 | 4.0-.667 |
| ECs Arterial | 10.0-70.0 | 1.01-.143 | .804-.114 | .402-0.0572 |

Within the patterned microgels, a tuned fluid flow is used to deliver biomimetic shear stress and cyclical stretch mechanical factors. During operation, the scale of these factors within the single channel co-culture chip is set by tuning the perfusion flowrate (shear stress) and lumen pressure (cyclical stretch). This tuning is realized in the single lumen system depicted in FIG. 5A of the main manuscript by optimizing the values of the critical pulmonary and aortic tuning resistors for specific target flow states. These resistor elements are varied through the inclusion of different lengths of tubing before (pulmonary) and after (aortic) the single lumen chip (FIG. 5A). The effect these tuning resistors have on flowrate through and gauge pressure within the perfusable lumen may be elucidated using a fluidic resistor capacitor model. This model is presented in the FIG. 5B. Within this model the pressure source (peristaltic pump) sets the pressure differential (ΔP) across the system. For a consistent applied pressure, the steady state flowrate through the device will be determined by the overall system resistance as per Ohms law.

$$Q = \frac{\Delta P}{R_{SYS}} \qquad \text{Equation 1}$$

Where Q is the volumetric flowrate through the system, ΔP is the pressure differential across the system and R_SYS is the system resistance. As is demonstrated by the equivalent circuit model for the system, all resistance elements within the model are in series with one another. As will be explored further below the resistance values for the pulmonary and aortic resistor elements should be significantly greater than that of any other system element in order to ensure uniform cyclic stretch within the microgel channel. As such RSYS can be simplified to.

$$R_{SYS} \approx R_P + R_A \qquad \text{Equation 2}$$

Where R_P is the resistance of the pulmonary element and R_A is resistance of the aortic element. The resistance of each tubing element may be calculated based on the dimensions and length of its lumen using:

$$R_H = \frac{8\eta L}{\pi R^4} \qquad \text{Equation 3}$$

Where L is the length of the tubing, R the radius or the lumen, η is the viscosity of the profusion liquid and R_H is the hydraulic resistance of the tubing. For the case of the single lumen device described in FIG. 2B the cross-sectional area of the lumens within the resistance tubing and the vessel chip are comparable. As such tubing lengths, at least an order of magnitude longer than the 1 cm lumen chip, is used for the pulmonary and aortic resistors. By combining equation 1, 2, and 3 the overall combined length of the aortic and pulmonary resistors desired to achieve a target flowrate is written as:

$$L_{sys} = \frac{\Delta P \pi R_{lumen}^4}{8\eta Q_{target}} \qquad \text{Equation 4}$$

Where L_SYS is the combined length of the aortic and pulmonary resistance tubing and Q_target is the target volumetric flowrate.

While the system resistance alone may be used to tune the flowrate through a device the pressure within a lumen may instead be set by the ratio between the aortic resistance and the overall system resistance. The gauge pressure of a point within a fluidic system can be determined by the fluidic circuit equivalent of the voltage divider equation $$P_{gauge} = \frac{\Delta P R_{ds}}{R_{SYS}} \qquad \text{Equation 5}$$

where P_gauge is the gauge pressure at the selected point, R_ds is the downstream resistance between the selected point and atmosphere, ΔP is pressure differential across the system, and R_sys is the resistance of the system. In order to estimate the gauge pressure within the microgel lumen using equation 5, the value of the aortic resistor may be used for the downstream resistance, and the sum of the aortic and pulmonary resistor values may be used for the system resistance. As such, using equations 3 we may rewrite equation 5 as $$P_{lumen} \approx \frac{\Delta P L_A}{L_{SYS}} \qquad \text{Equation 6}$$

Where P_lumen is the lumen gauge pressure, L_A is the length of the aortic resistor and L_SYS is the combined length of aortic and pulmonary element. For simplicity the ratio between the lengths of the aortic and system resistances can be labeled the Pressure Correction Factor or PC. This approach discounts the pressure differential across the microgel lumen. This may be done as the as the resistance of this component is designed to be minimal in comparison to the system resistance. As a result, there is only a negligible pressure differential across the microgel lumen yielding relatively uniform gauge pressure within. This uniformity is useful to obtain similar degrees of cyclical stretch along the length of the co-culture channel.

As is evident from equations 1 and 6, by carefully optimizing the lengths of the Aortic and Pulmonary elements, the PC and R_sys values may be set independently of each other. As is demonstrated in FIG. 5C, which plots stable gauge pressure and for a range of R_SYS values and set PC values, this allows for precise tuning of the flowrate and pressure within the lumen.

Figure 6A:
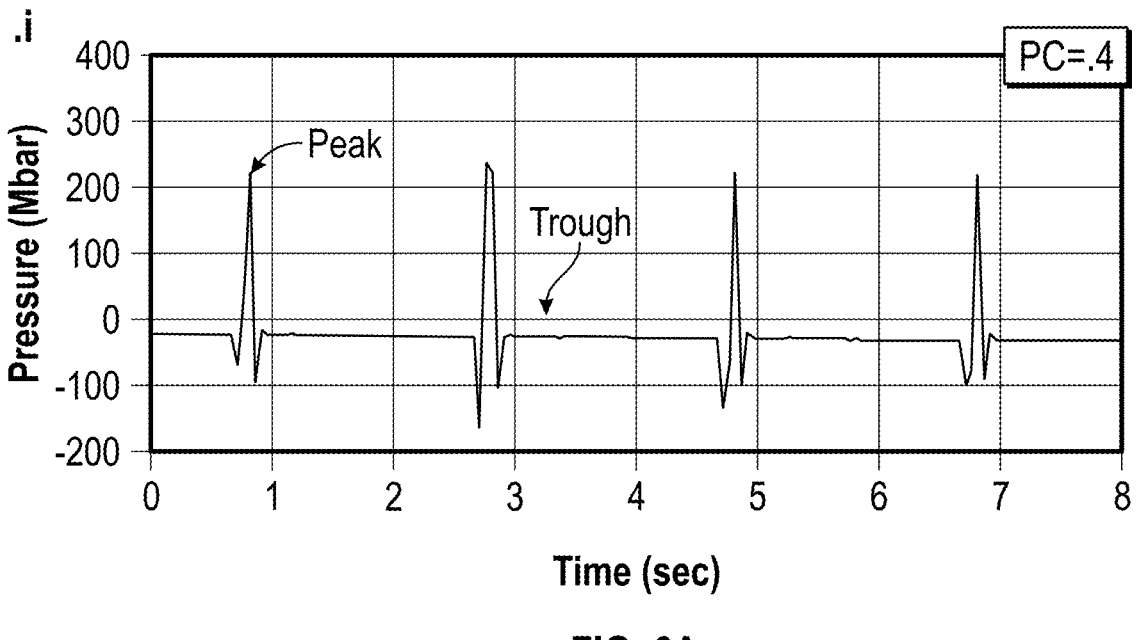
FIGS. 6A-6B illustrate graphs of a pressure signal.
Figure 6B:
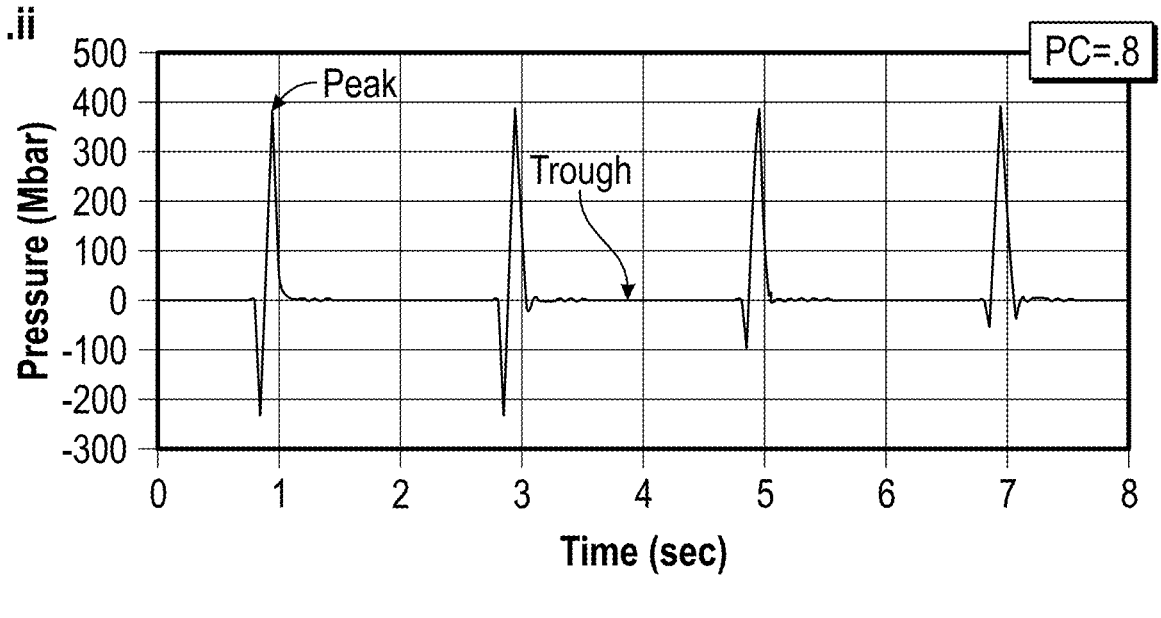
Figures 10A, 10B, 10C:
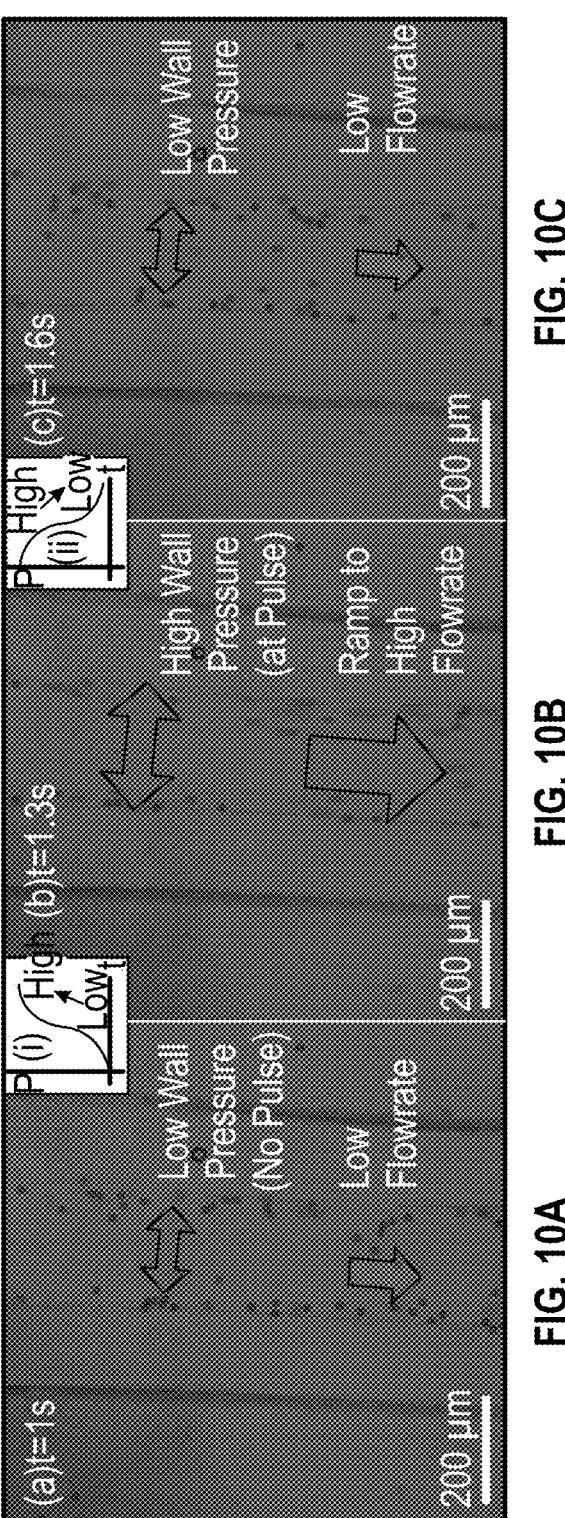
FIGS. 10A-10C illustrate images of a hydrogel channel experiencing shear stress due to flow rate variations.

As described above, in order to demonstrate delivery of cyclic stretch within a microgel environment, a perfusable single lumen hydrogel microfluidic device featuring a compliable PDMS superstructure is prepared. This device is then perfused using the fluidic system outlined in FIG. 5A. As is described in detail above, lengths of tubing for the pulmonary and aortic resistors are selected such that the pressure correction factor (PC) is set to 0.4 and 0.8. Once assembled the system is perfused using a peristaltic pump and the Lumen pressure signal is measured using an inline pressure sensor positioned on aortic side of the perfusable hydrogel vessel. FIGS. 6A-6B shows the resulting pressure signal featuring 240 Mbar peaks for a PC value of 0.4 (FIG. 6A) and 400 Mbar peaks for a PC value of 0.8 (FIG. 6B) with peaks separated by 2 second ground pressure troughs for both cases.

FIGS. 7A-7D illustrate isolated brightfield images of perfused lumen from peak and trough timepoints for a PC value of 0.4 where FIG. 7A shows the trough and FIG. 7B shows the peak. FIGS. 7C-7D illustrate the same for a PC value of 0.8 where FIG. 7C illustrates a trough and FIG. 7D illustrates a peak. Lumen diameter can be monitored optically during profusion and bright field video is captured. From the resulting video, frames of the lumen at signal trough and peak time points are isolated. Using image processing software (ImageJ) the θ position of the lumen can be normalized and four lumen diameter measurements can be taken along the length of the lumen to determine minimum (FIG. 7A for PC=0.4 and FIG. 7B for PC=0.8) and maximum (FIG. 7C for PC=0.4 and FIG. 7D for PC=0.8) lumen diameter.

These measured minimum and maximum lumen diameter values for PC values of 0.4 and 0.8 are measured, as shown in FIGS. 8A-8D, and are presented below in Table 2.

Percent cyclic stretch along the outside of a lumen can be estimated as the percentage increase in lumen diameter during a pressure pulse. From the measured values the average increase in lumen diameter for a pressure pulse tuned with a PC value of 0.4 is estimated as 43.4 μm. This yields an estimated percent cyclic stretch value of 5.9%. For a pressure pulse tuned with a PC value of 0.8 the average increase in diameter is estimated as 81.3 μm. This yields an estimated percent cyclic stretch value of 11%.

Lithographic Alignment

The alignment and reversible bonding of the lumen imprint and the shell microchannel can be achieved by a modified large gap alignment process, using a standard mask aligner (EV Group 620). The PDMS microchannel component can be first mounted onto a 4-inch square soda lime glass plate, which can then be loaded into the aligner such that it is face down towards the chuck, where the PDMS insert core component can be loaded. To ensure uniform separation during alignment and contact during temporary bonding, prior to loading the imprint core, a wedge error correction (WEC) process can be run to parallelize the chuck, on which the core component can be loaded with the glass plate and on which the channel component can be already mounted. To limit damage to the channel component during this process, a frame can be loaded in between the glass plate and chuck to allow the WEC pressure to be applied between the glass plate and the chuck, such as without requiring the loaded core component to come into contact with the chuck. After the WEC step, the imprint core can be loaded onto the chuck and can be aligned to the channel using alignment marks. Due to the topography of the imprint core, a separation gap of 1 mm can be used during the alignment step. The software of the large gap alignment setting can allow for alignment of features that are not in the same focal plane. After the initial alignment step is finished, the channel can be gradually lowered onto the insert, with fine corrections to alignment being made as the two components are brought into close proximity with one another. Once assembled, pressure can be applied to form a reversible bond between the two PDMS components, which can then be unloaded from the mask aligner.

Channel Fabrication

The outer PDMS channel and lumen imprint can be replicated from either a SU-8 mold or 3D printed masters constructed using a standard soft lithography process. Negative master molds of both components can be prepared using either SU-8 photolithography or 3D printing. In the case of the SU-8 on silicon masters, an anti-stiction silane layer can be vapor deposited to improve mold release. Rigidity of the PDMS components can be tailored by their base to curing agent ratio and curing temperature according to their function. For the imprint components, where higher rigidity can be used to ensure pattern fidelity, a 10 to 3 base to curing agent ratio can be used and the molds can be cured on a covered hotplate for 3 hours at 120° C. The lumen imprint

| | m1 | m2 | m3 | m4 | Average |
|---|---|---|---|---|---|
| PC = .4 | | | | | |
| Min. Lumen Dia. (μm) | 739.7959 | 733.4184 | 736.6071 | 739.7959 | 737.4043 |
| Max. Lumen Dia. (μm) | 779.6556 | 781.25 | 776.4668 | 786.0332 | 780.8514 |
| PC = .8 | | | | | |
| Min. Lumen Dia. (μm) | 736.6071 | 739.7959 | 733.4184 | 738.2015 | 737.0057 |
| Max. Lumen Dia. (μm) | 817.9209 | 813.1378 | 821.1097 | 821.1097 | 818.3195 | components can be then treated with a 1% BSA solution for 15 minutes at room temperature, before blow drying with a high-pressure dry nitrogen source. Microchannels used in applications not designed for replicating cyclical stretch can be produced by the same protocol, with the exception of the anti-stiction layer. Instead, if GELMA is used for the microgel structure, a methacrylated silane adhesion layer can be deposited on the channel device. In cases where cyclic stretch is recapitulated, a lower rigidity can be used to allow the microgels to deform under the high lumen pressures. Hence, a 20 to 1 base to curing agent ratio for PDMS can be used and cured at room temperature for 24 hrs.

Fluidic Perfusion and Mechanical Measurements

For applications that do not investigate cyclical stretch, the PDMS superstructure with the microgels can be sealed by using a 3D printed scaffold to sandwich the device between two glass plates. The PDMS chip can form a reversible physical bond with the glass plate sealing the channel, while the 3D printed scaffold can apply sufficient pressure to ensure that the bond withstands the lumen pressure during perfusion. To deliver fluid, flow inlet or outlets can be drilled though one of the glass plates to allow for tubing to be inserted within the PDMS device. For cases where higher compliance PDMS is used to facilitate cyclical stretch of microchannels during pulsed perfusion, an adhesive bonding method can be used to bond a glass slide to the PDMS chip. After bonding, biomimetic temporal and mechanical factors can be introduced by perfusing the channel with a peristaltic pump.

Endothelial Cell Culture in Perfusable Microgel

To study the effects of the perfusable microgel on endothelial cell (EC) viability and morphology, dermal EC's can be seeded and cultured under fluid flow for 24 hours. Dermal endothelial cells (Cell Biologics) can be expanded (4 passages-7 passages) in T-25 plates coated with gelatin 2%. Cell expansion can be done using endothelial cell medium (e.g., Cell Biologics cat #C57-6064). Once confluency is reached, cells can be plated out using, for example, TrypLE 10x (Fisher Scientific) and can then be seeded within a microgel channel at a cell density of 105 cells per mL. The perfusable microgel channel prepared using the methods outlined in FIG. 2, discussed above, featured a 1 cm long 375 µm high and 750 µm wide microgel structure aligned within a PDMS superstructure with a 250 µm high and 480 µm wide perfusable lumen. The structure can be made of a 10% gelatin (enzymatically crosslinked by microbial transglutaminase or mTG). Post seeding, the cells can be left in static conditions for 4 hours within the microgel channel such as to allow them to attach to the gel surface, after which a 600 µl/min fluid flow can be delivered to the system using a peristaltic pump. A no-flow static condition device can also be prepared where the cells can be seeded in an open channel submerged within 5 mL of media. After 24 hours cell morphology can be imaged using, for example, an EVOS FL (life technologies) for both devices. The shear stress incident on the cells cultured within the device can be estimated at 17.8 dynes/cm2, which is at the lower end of the reported physiological range (15 to 150 dynes/cm2).

Microfluidic imprint lithography (MIL) can be used to fabricate high resolution perfusable microgel channels that can be integrated within a PDMS superstructure to deliver biomimetic spatio-temporal fluidic cues to cells and tissues in 3D culture systems. Utilizing the MIL method, a range of possible microgel structures can be created, including those that maintain the spatial component of mass transport from vasculature, strategies to pattern interfaces of multiple biomaterials, and highly versatile liquid-to-gel and gel-to-gel interfaces. Since these perfusable microgels can be integrated within microfluidic channels, important mechanical factors, such as shear stress and cyclical stretch can also be delivered. By embedding the perfusable microgels in a compliant PDMS superstructure, the microgel channel can exhibit biomimetic levels of cyclic stretch upon being pressurized under fluid flow cues and can exhibit shear stress under flow rate cues. This feature can be used for orthogonal alignment of endothelial to smooth muscle cells, akin to their arrangement within micro-vasculatures. Although the present disclosure discusses only the replication of flow cues at the top end of the physiological range, the integrated gel-PDMS devices can be used with other microfluidic methods for delivery of lower scale fluidic flow rates and pressures.

Further Discussion

FIGS. 9A and 9B illustrate a process to fabricate channels in hydrogel, per the sequence shown in FIGS. 9H-9J, along with the ability for fluidics (as shown in FIG. 9C) and "wet" alignment (as shown in FIG. 9D). Example hydrogel channels are shown in FIGS. 9E and 9F, while fluidic pulsing with sample beads are shown in FIG. 9G to demonstrate perfusion ability.

One example of a process can include constructing fluidic channels within the hydrogel as shown in FIGS. 9H-9J by using a patterned mold to imprint into the spatially confined gelatin hydrogel layer (as shown in FIGS. 9A and 9B) for creating the shell with an open core. PDMS spacers can serve as scaffold to determine channel wall dimensions, as well as to enable fluidic interfaces into the channel that is created in the hydrogel (FIG. 9C) and for "wet" lithographic alignment, but importantly, the cells are not in contact with the PDMS interfaces.

Upon release after the steps shown in FIGS. 9H-9J, a core-shell structure as per FIGS. 9E-9F can be obtained. The core can be interfaced for enabling fluidic control (as shown in FIG. 9C), as apparent from flowing beads in FIG. 9G. An initial example of the patterned of cell-laden hydrogel obtained by imprint lithography is shown in FIG. 9D, which shows that it is possible to create free standing 200 µm structures without a significant residual layer. Using beads in the fluid, FIGS. 10A-10D shows how the pulse flow can modulate the wall pressure and shear flow, which is currently being explored using various types of fluids pulsating and flows.

A core-shell hydrogel structure can be fabricated by lithography to serve as a template for aligning cell topologies within each patterned shell, alongside an open core that is designed for implementing desired fluidic cues. In this manner, cells in the hydrogel are placed against materials of stiffness encountered in vivo and can be influenced by physiologically relevant fluidic cues that can be modulated based on wall compliance and induced wall shear stress in the hydrogel.

Additional Details

The development in vitro tissue models that recapitulate the complex physiological environment and cues present within in vivo tissues has been widely recognized as a core potential of lab-on-a-chip platforms. Due to resource needs and ethical considerations involved with animal models, in vitro testing is often considered an important first step for a diverse range of applications, such as drug testing, regenerative medicine, tissue engineering, and disease models in bioengineering. While tremendous advances have occurred over the last decade in the biomanufacturing of tissue constructs, there remains a large gap between in vitro tissue models and development of constructs with clinically relevant scale that are sufficient for tissue implantation. A technological barrier to development of more native-like in vitro tissue models and clinically-relevant implantable biomimetic tissues is the lack of physiologically relevant resistance vessels ($\approx$100-200 μm) and microvasculature (arterioles ($\approx$100 μm or less and capillaries $\approx$5-10 μm). Specifically, the ability to modulate flow conditions is critical for delivery of nutrients and removal of waste to build and maintain functional 3D cell and biomimetic tissue cultures. Another feature to microvascular regulation and function is the intimate juxtaposition of the endothelial lining of vessels and the underlying smooth muscle cell layer.

Vascular systems offer biofunctional cues the extend beyond their ability to improve mass transport due to perfusable lumen and their surrounding tissue. The role of mechanical factors associated with pressure driven blood flow on surrounding tissue has been elucidated. Alignment of endothelial cells due to sheer stress induced by blood flow plays an important role in the formation of the endothelial barrier function between the vasculature lumen and surrounding tissues, with its disruption leading to a 'leaky' endothelial barrier. On the other hand, smooth muscle cells within vasculatures are orthogonally aligned to ECs and sheer stress can cause them to undergo apoptosis. Hence, limiting the effects of sheer stress on neighboring cell types, while continuing to deliver an adequate profusion rate to facilitate mass transport requires spatially tailored flow profiles within the perfusable lumen, so that the flow conditions replicate either homeostasis or the disease state under investigation. Another factor that influences the mechanical cues delivered to cells in 3D culture is the lumen pressure. Pulsatile fluid flow delivered to the relatively elastic arteries, veins and surrounding tissues, results in an increase in lumen diameter over short durations. This cyclical stretch of surrounding tissues has been demonstrated to not only influence endothelial cell configuration, but also align perivascular cells, such as smooth muscle cells. Transmural pressure, the pressure differential from the vessel lumen across surrounding tissue, has also been shown to influence endothelial cell sprouting, independent of cyclical stretch from lumen diameter increase.

A core element for replicating the mechanical factors associated with fluid flow in vitro is the ability to widely vary blood flow rates and profiles over the multiscale vascular network. Driven by the heart blood, flow is pulsatile in large diameter vessels, such as arteries and veins. However, the elastic nature of these vessels dampens such pressure pulses, leading to successively less pulsatile steady state flow to the downstream capillary systems. The lumen diameter of vessels and the volumetric flowrate of blood flow through them varies greatly throughout the circulatory system. These have an effect on the shear stress incident on the endothelial wall, which varies broadly, with a reported range of 1 dynes/cm$^2$ to 6 dynes/cm$^2$ for veins and 10 dynes/cm$^2$ to 70 dynes/cm$^2$ for arteries. The direction and uniformity of such shear stress may also vary throughout the body, as blood flow in straight channels is laminar, but can become disturbed at branches or regions with sharp turns. In such cases variations in EC alignment have been demonstrated.

As shown in FIG. 1, the ability to independently control perfusion flow rate, lumen pressures, and temporal flow profiles with a high degree of spatial resolution is central towards recapitulating vascular factors of relevance to in vitro models of different homeostatic and disease states within 3D culture systems. Microfluidic systems based on PDMS (poly-di-methyl siloxane) offers a diverse range of methods for facile flow and pressure control, as well as multiple platforms for recapitulating complex physiological flow states. The present disclosure seeks to integrate hydrogel materials within a fluidic channel to enable perfusion.

Fabrication of micropatterned hydrogels (henceforth called microgels) in the form of perfusable channels or lumen for enabling their facile integration with fluidic control systems, on one hand, and to cell-laden biomaterials, on the other hand, allow for spatially and temporally controlled fluidic cues to be delivered to cells and tissues within the 3D culture. These methods and devices combine microfluidic and imprint lithography methods to pattern these microgels as high-resolution lumens. The present disclosure makes use of microfluidic imprint lithography method (MIL) using the high tolerance and reversible nature of the bond alignment process to lithographically position imprints within a microfluidic device to enable the filling and patterning of lumens of microgels, thereby leveraging the benefits of both parent processes. PDMS microfluidic channels, which can be fabricated at high-resolution by micromolding into lithographically patterned SU8 resists are used to bound the outer dimension of the microgel lumen, while other PDMS imprint structures can shape the inner dimension of the microgel lumen to create groove, channel, or internal patterns. Following patterning, the resulting microgel structure can either be released from the microfluidic channel to create stand-alone structures or can remain inside the scaffolding provided by PDMS superstructure, so that each lumen can be individually addressed by fluidic cues. The PDMS superstructure also can act to reinforce the microgel lumen structure to allow for perfusion to deliver materials at physiologically relevant flow rates and pressures. Specifically, this disclosure discusses the ability of the MIL method to fabricate microgel lumen structures with single or multiple shells and its fluidic interfacing to deliver physiologically relevant mechanical cues for recapitulating shear stress and cyclical stretch factors. In this manner, not only does the method create the bio-functionality and topology of micro-vasculatures, but also creates important features of relevance to biological flow, such as the ability for pulsation, modifiable wall compliance, and induced wall shear stress, thereby creating the cues to recapitulate microvasculature growth in patterned and perfusable 3D culture systems.

Microfluidic Imprint Lithography Process

FIG. 11 illustrates a process flow for fabrication of single lumen structures. The process of FIG. 11 can be similar to the process of FIG. 2A, where additional details are shown with respect to FIG. 11.

To fabricate a device 1100 including a perfusable micronscale hydrogel structure (microgel) 1106 integrated within a PDMS superstructure 1102, a combined microfluidic patterning and aligned imprinting processes can be used. This so-called microfluidic imprint lithography (MTh) method can use a PDMS core imprint 1104 component to define the perfusable lumen of the microgel (as shown in FIGS. 11A-11H). The PDMS core imprint 1104 can be then aligned using the process outlined below and is inserted into a shell microchannel 1101 of a superstructure 1102, which defines the microgel's outer diameter and also acts as structural reinforcement for perfusion. Pressure can be applied such that the lumen imprint 1104 is reversibly bonded to the channel 1102 to create an enclosed microchannel, which defines the dimensions of the microgel. Hydrogel 1106 (composed of gelatin methacrylate or GELMA) is introduced into the microchannel by syringe pump and cured using the UV crosslinking method to form the microgel. In order to improve adhesion of the gel within the microchannel, a methacrylate silane layer is deposited on the shell microchannel prior to alignment. The core imprint 1104 can then de-bonded to define a lumen 1108 of the hydrogel lined microfluidic channel. In order to facilitate a clean release and prevent damage to the microgel pattern, the PDMS core imprint 1104 can be treated with a 1% BSA solution to act as an anti-stiction layer. After release, the channel 1101 and lumen 1108 can be sealed (such as with a glass slide 1109) to form a perfusable microgel embedded in a PDMS superstructure.

Alignment Process

The alignment and reversible bonding of the lumen imprint and the shell microchannel can be achieved by a modified large gap alignment process, using a standard mask aligner (e.g., EV Group 620). The PDMS microchannel component can first be mounted onto a 4-inch square soda lime glass plate, which can then be loaded into the aligner such that it is face down towards the chuck, where the PDMS insert core component can be loaded. To help ensure uniform separation during alignment and contact during temporary bonding, prior to loading the imprint core, a wedge error correction (WEC) process can be run to parallelize the chuck, on which the core component will be loaded with the glass plate and on which the channel component has already been mounted. To limit damage to the channel component during this process, a frame can be loaded in between the glass plate and chuck to allow the WEC pressure to be applied between the glass plate and the chuck, without necessitating that the loaded core component come into contact with the chuck. After the WEC step, the imprint core can be loaded onto the chuck and aligned to the channel using alignment marks. Due to the topography of the imprint core, a separation gap of 1 mm should be maintained during the alignment step. This alignment process is greatly simplified by using a large gap alignment process, which allows for alignment of features not in the same focal plane. After the initial alignment step is finished, the Channel is slowly lowered onto the insert, with fine corrections to alignment being made as the two components are brought into close proximity with one another. Once assembled pressure is applied to form a reversible bond between the two PDMS components, which are then unloaded from the mask aligner.

Multi Material Microfluidic Imprint Lithography Process

Figure 12A:
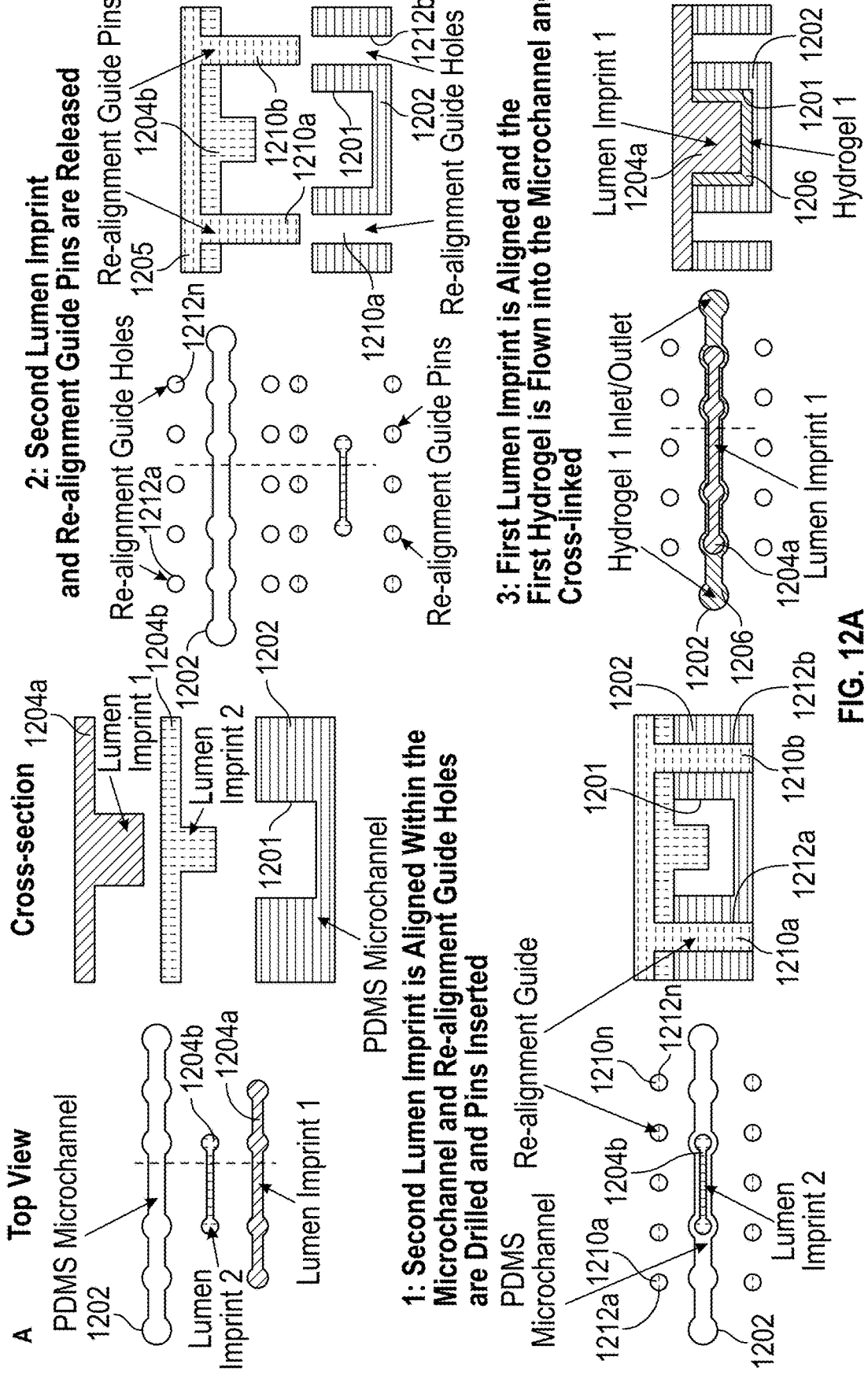
FIG. 12A illustrate schematics of a process flow for fabricating devices.
Figure 12C:
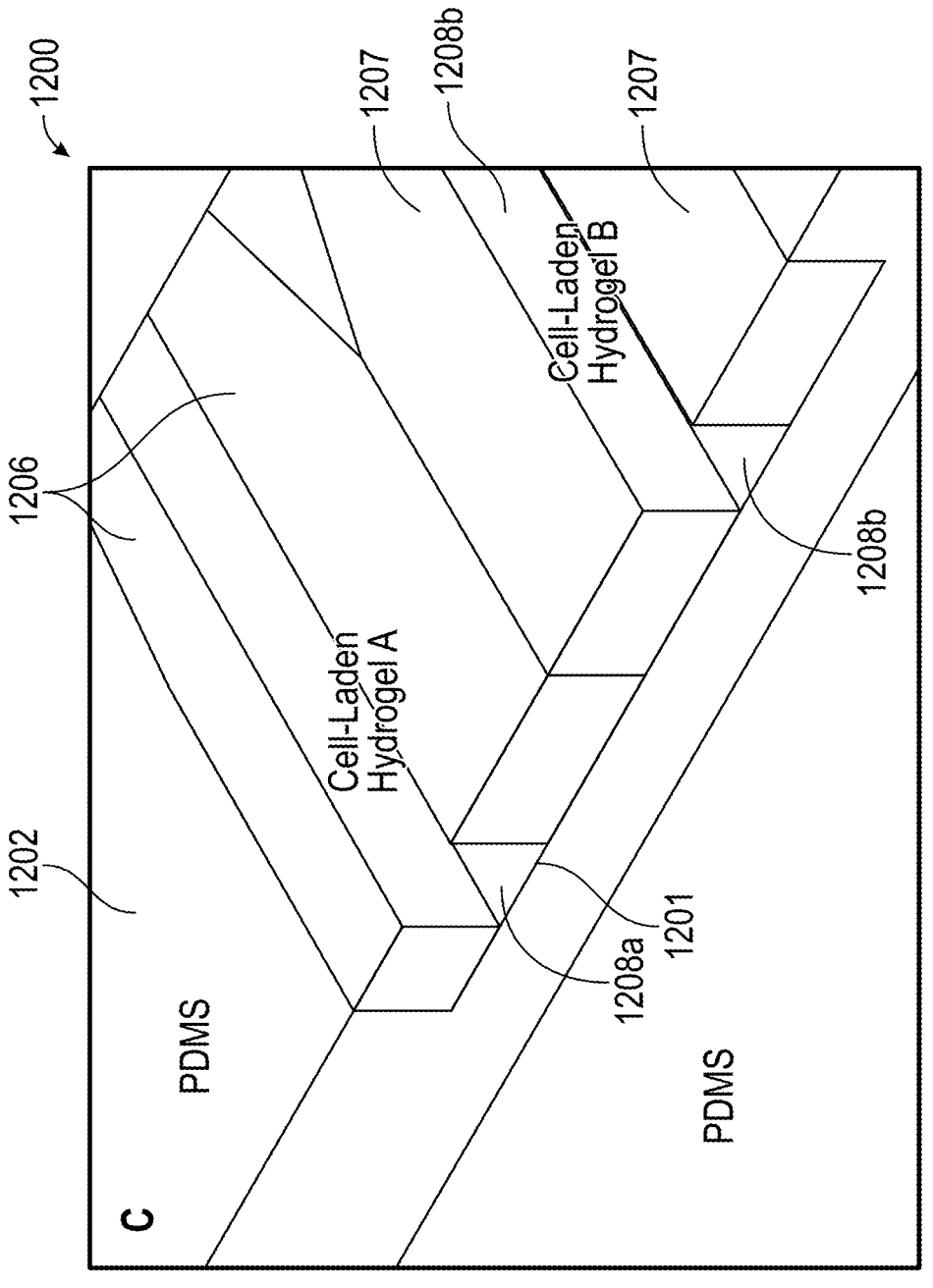
FIG. 12C illustrates a cut away 3D model of a final device resulting from the process outlined in FIG. 12B.

FIG. 12A illustrates schematics of a process flow for fabricating devices requiring multiple imprints utilizing the 3d printed realignment rig. FIG. 12B illustrates schematics of a process flow for patterning a microgel featuring an interface between two biomaterials. FIG. 12C illustrates a cut away 3D model of a final device resulting from the process outlined in FIG. 12B. FIGS. 12A-12C are discussed together below. The process discussed with respect to FIG. 12 can be similar to the process discussed with respect to FIG. 3. Additional details are shown in FIG. 12A.

It is possible to fabricate complex perfusable microgels with multiple patterned biomaterial structures by repeating the process outlined above with a second imprint component, however a modified alignment process can be used, in such cases. As the alignment process outlined above takes 10-20 minutes, depending on the complexity of the pattern, it can be difficult to use this process after the initial biomaterial structure has been formed due to desiccation of the hydrogel. In order to overcome this constraint, a method to rapidly re-align previously aligned core and shell components can be used, as shown in FIG. 12A. In this process a second imprint component 1204*b* can be aligned to a microchannel 1201 of a superstructure 1202 first by the methods outlined above with respect to FIG. 11.

After the reversible bonding step, re-alignment guide holes 1210*a*-1210*n* can be drilled through two aligned components (e.g., the superstructure 1202 and a second imprint 1204*b*) in a configuration set by a 3D printed holder, using a biopsy punch. The aligned components can then be mounted on a 3D printed scaffold 1205 using pins 1210*a* and 1210*b* that correspond to the layout of drilled alignment holes. The channel 1201 can then be released, leaving the imprint core 1204 still mounted on the scaffold 1205. The first microgel patterning step can then be completed as outlined above using a first imprint 1204*a*. After a first microgel 1206 has been formed, the channel 1201 is then rapidly re-aligned to the second imprint core 1204*b* by mounting it back on the scaffold using the pins 1210*a*-1210*n* and the alignment holes 1212*a*-1212*n*. A second biomaterial 1207 may then be filled into the device and crosslinked to form a multi-material microgel structure.

Channel and Insert Fabrication

The outer PDMS channel and lumen imprint can be replicated from either a SU-8 mold or 3D printed masters constructed using a standard soft lithography process. Negative master molds of both components are prepared can use either Su-8 photolithography or 3d printing. In the case of the Su-8 on silicon masters an anti-stiction silane layer can be vapor deposited to improve mold release. Rigidity of the PDMS components can be tailored by their base to curing agent ratio and curing temperature according to their function. For the imprint components, where higher rigidity is helpful to ensure pattern fidelity, a 10 to 3 base to curing agent ratio can be used and the molds can be cured on a covered hotplate for 3 hours at 120° C. The lumen imprint components can then be treated with a 1% BSA solution for 15 minutes at room temperature, before blow drying with a high-pressure dry nitrogen source. Microchannels used in applications that are not designed for replicating cyclical stretch can be produced by the same protocol, with the exception of the BSA anti-stiction layer, which is not applied. Instead, if GELMA is being used for the microgel structure, a methacrylated silane adhesion layer can be deposited on the channel device. In cases where cyclic stretch is being recapitulated, a lower rigidity can be used to allow the microgels to deform under the high lumen pressures, therefore a 20 to 1 base to curing agent ratio for PDMS can be used and cured at room temperature for 24 hrs.

Profusion and Mechanical Cue Measurement

For applications that do not investigate cyclical stretch, the PDMS superstructure with the microgels can be sealed by using a 3D printed scaffold to sandwich the device between two glass plates. The PDMS chip can form a reversible physical bond with the glass plate sealing the channel, while the 3D printed scaffold can apply sufficient pressure to ensure that the bond withstands the lumen pressure during perfusion. In order to deliver fluid, flow inlet/outlets can be drilled though one of the glass plates to allow for tubing to be inserted within the PDMS device. For cases wherein higher conformity PDMS can be used to facilitate cyclical stretch of microchannels during pulsed perfusion, an adhesive bonding method can be used to bond a glass slide to the PDMS chip. After bonding, biomimetic temporal and mechanical factors can be introduced by perfusing the channel with a peristaltic pump. The flow rate and gauge pressure within the perfusable microgels can be tuned to match physiological levels through the use of upstream/downstream tuning resistances (FIG. 2D). The flow rate can be set by tailoring the total value of the system resistance, while the lumen gauge pressure can be set by the ratio between the resistance upstream and downstream of the device, as described subsequently.

NOTES AND EXAMPLES

The following, non-limiting examples, detail certain aspects of the present subject matter to solve the challenges and provide the benefits discussed herein, among others.

Example 1 is a microfluidic device comprising: a super-structure defining a microfluidic channel therein; a first hydrogel releasably bonded to the microfluidic channel to define a perfusable channel therein, the first hydrogel including cells embedded therein or thereon.

In Example 2, the subject matter of Example 1 optionally includes a second hydrogel bonded to the microfluidic channel and to the first hydrogel to define a second perfusable channel therein.

In Example 3, the subject matter of Example 2 optionally includes wherein the second hydrogel is of a different biomaterial than the first hydrogel.

In Example 4, the subject matter of any one or more of Examples 1-3 optionally include a second hydrogel bonded to the first hydrogel to define, together with the first hydrogel, the perfusable channel.

In Example 5, the subject matter of Example 4 optionally includes wherein the second hydrogel is of a different biomaterial than the first hydrogel.

In Example 6, the subject matter of any one or more of Examples 1-5 optionally include a second hydrogel bonded to the microfluidic channel and spaced away from the first hydrogel to form, together with the first hydrogel, the perfusable channel.

In Example 7, the subject matter of Example 6 optionally includes wherein the second hydrogel is of a different biomaterial than the first hydrogel.

In Example 8, the subject matter of any one or more of Examples 1-7 optionally include wherein the first hydrogel is a microgel structure.

In Example 9, the subject matter of any one or more of Examples 1-8 optionally include wherein the first hydrogel is patterned to mimic organic tissue.

In Example 10, the subject matter of any one or more of Examples 1-9 optionally include wherein the first hydrogel is patterned to mimic vascular endothelial cells or smooth muscle cells.

In Example 11, the subject matter of any one or more of Examples 1-10 optionally include wherein the superstructure is made of poly-di-methyl siloxane.

Example 12 is a method of forming a hydrogel microfluidic perfusable channel, the method comprising: providing a microchannel in a superstructure; forming a channel imprint; aligning the channel imprint with the microchannel of the superstructure; bonding, releasably, the channel imprint to the superstructure; bonding, a first hydrogel to the channel imprint and the microchannel of the superstructure form a perfusable channel in the first hydrogel; and de-bonding the imprint from the first hydrogel and the superstructure; and removing the channel imprint from the superstructure.

In Example 13, the subject matter of Example 12 optionally includes applying an anti-stiction layer to the superstructure before bonding the channel imprint to the superstructure.

In Example 14, the subject matter of any one or more of Examples 12-13 optionally include applying a methacrylate silane layer to the microchannel before bonding the first hydrogel to the microchannel.

In Example 15, the subject matter of any one or more of Examples 12-14 optionally include wherein the first hydrogel is formed using ultraviolet crosslinking.

In Example 16, the subject matter of any one or more of Examples 12-15 optionally include aligning a second channel imprint with the microchannel of the superstructure; bonding the second channel imprint to the superstructure; forming alignment holes in the superstructure; and de-bonding the second channel imprint from the superstructure before aligning the channel imprint to the superstructure.

In Example 17, the subject matter of Example 16 optionally includes aligning the second channel imprint with the microchannel of the superstructure using the alignment holes; and bonding, a second hydrogel to the second channel imprint.

In Example 18, the subject matter of Example 17 optionally includes wherein the second hydrogel is of a different biomaterial than the first hydrogel.

In Example 19, the subject matter of any one or more of Examples 17-18 optionally include wherein the second hydrogel is bonded to the first hydrogel to define, together with the hydrogel, the perfusable channel.

In Example 20, the subject matter of any one or more of Examples 17-19 optionally include wherein the second hydrogel is bonded to the microchannel and spaced away from the first hydrogel to form, together with the first hydrogel, the perfusable channel.

In Example 21, the subject matter of any one or more of Examples 17-20 optionally include wherein the second hydrogel is bonded to the microchannel and to the first hydrogel to define a second perfusable channel therein.

In Example 22, the subject matter of any one or more of Examples 12-21 optionally include wherein the first hydrogel forms a microgel structure.

In Example 23, the subject matter of Example 22 optionally includes wherein the first hydrogel is patterned to mimic organic tissue.

In Example 24, the subject matter of any one or more of Examples 22-23 optionally include wherein the first hydrogel is patterned to mimic vascular endothelial cells or smooth muscle cells.

In Example 25, the subject matter of any one or more of Examples 12-24 optionally include wherein the superstructure is made of poly-di-methyl siloxane.

Example 26 is a method for one or more of the following: a) providing perfusable core-shell hydrogels for 3D cultures with physiologically-relevant microvascular cues, b) creating micro-physiological transport cues to in vitro 3D culture of cells using microfluidic imprint fabrication, c) providing patterned and perfusable core-shell hydrogels for 3D cultures with micro-physiological transport cues, d) providing microfluidic imprint fabrication of patterned and perfusable cell-laden hydrogels for 3D culture, or e) providing perfusable cell-laden micropatterned hydrogels for spatio-temporal vascular-like cues to tissues, as described herein.

In Example 27, the subject matter of any one or more of Examples 16-26 optionally include one or more feature or combination of features disclosed herein.

Example 28 is a system for providing one or more of the following: a) perfusable core-shell hydrogels for 3D cultures with physiologically-relevant microvascular cues, b) creation of micro-physiological transport cues to in vitro 3D culture of cells using microfluidic imprint fabrication, c) patterned and perfusable core-shell hydrogels for 3D cultures with micro-physiological transport cues, d) microfluidic imprint fabrication of patterned and perfusable cell-laden hydrogels for 3D culture, or e) perfusable cell-laden micropatterned hydrogels for spatio-temporal vascular-like cues to tissues, as described herein.

In Example 29, the subject matter of Example 28 optionally includes one or more feature or combination of features disclosed herein.

Example 30 is a computer-readable storage medium having computer-executable instructions stored thereon which, when executed by one or more processors, cause one or more computers to perform functions for performing one or more of the following: a) providing perfusable core-shell hydrogels for 3D cultures with physiologically-relevant microvascular cues, b) creating micro-physiological transport cues to in vitro 3D culture of cells using microfluidic imprint fabrication, c) providing patterned and perfusable core-shell hydrogels for 3D cultures with micro-physiological transport cues, d) providing microfluidic imprint fabrication of patterned and perfusable cell-laden hydrogels for 3D culture, or e) providing perfusable cell-laden micropatterned hydrogels for spatio-temporal vascular-like cues to tissues, as described herein.

In Example 31, the subject matter of Example 30 optionally includes one or more feature or combination of features disclosed herein.

In Example 32, the apparatuses or method of any one or any combination of Examples 1-31 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A microfluidic device comprising:
a superstructure defining a microfluidic channel therein; and
a first hydrogel releasably bonded to all sides of the microfluidic channel to define a perfusable channel therein, the first hydrogel including cells embedded therein, the first hydrogel patterned to mimic organic tissue.

2. The microfluidic device of claim 1, further comprising:
a second hydrogel bonded to the microfluidic channel and to an internal surface of the first hydrogel to define a second perfusable channel therein that is coaxial to the perfusable channel.

3. The microfluidic device of claim 2, wherein the second hydrogel is of a different biomaterial than the first hydrogel.

4. The microfluidic device of claim 1, further comprising:
a second hydrogel bonded to the first hydrogel to define, together with the first hydrogel, the perfusable channel.

5. The microfluidic device of claim 4, wherein the second hydrogel is of a different biomaterial than the first hydrogel.

6. The microfluidic device of claim 1, further comprising:
a second hydrogel bonded to the microfluidic channel and spaced away from the first hydrogel to form, together with the first hydrogel, the perfusable channel.

7. The microfluidic device of claim 6, wherein the second hydrogel is of a different biomaterial than the first hydrogel.

8. The microfluidic device of claim 1, wherein the first hydrogel is a microgel structure.

9. The microfluidic device of claim 1, wherein the first hydrogel is patterned to mimic vascular endothelial cells or smooth muscle cells.

10. The microfluidic device of claim 1, wherein the superstructure is made of poly-di-methyl siloxane.

11. A method of forming a hydrogel microfluidic perfusable channel, the method comprising:
providing a microchannel in a superstructure;
forming a channel imprint;

aligning the channel imprint with the microchannel of the superstructure;

bonding, releasably, the channel imprint to the superstructure;

bonding, a first hydrogel to the channel imprint and the microchannel of the superstructure form a perfusable channel in the first hydrogel;

de-bonding the channel imprint from the first hydrogel and the superstructure; and removing the channel imprint from the superstructure.

12. The method of claim 11, further comprising:

applying an anti-stiction layer to the superstructure before bonding the channel imprint to the superstructure.

13. The method of claim 11, further comprising:

applying a methacrylate silane layer to the microchannel before bonding the first hydrogel to the microchannel.

14. The method of claim 11, wherein the first hydrogel is formed using ultraviolet crosslinking.

15. The method of claim 11, further comprising:

aligning a second channel imprint with the microchannel of the superstructure;

bonding the second channel imprint to the superstructure;

forming alignment holes in the superstructure; and de-bonding the second channel imprint from the superstructure before aligning the channel imprint to the superstructure.

16. The method of claim 15, further comprising:

aligning the second channel imprint with the microchannel of the superstructure using the alignment holes; and bonding, a second hydrogel to the second channel imprint.

17. The method of claim 16, wherein the second hydrogel is bonded to the first hydrogel to define, together, the perfusable channel.

18. The method of claim 16, wherein the second hydrogel is bonded to the microchannel and spaced away from the first hydrogel to form, together with the first hydrogel, the perfusable channel.

19. The method of claim 16, wherein the second hydrogel is bonded to the microchannel and to the first hydrogel to define a second perfusable channel therein.

20. A microfluidic device comprising:

a superstructure defining a microfluidic channel therein;

a first hydrogel releasably bonded to all sides of the microfluidic channel to define a perfusable channel therein, the first hydrogel including cells embedded therein; and a second hydrogel bonded to the first hydrogel to define, together with the first hydrogel, the perfusable channel.

* * * * *